(12) United States Patent
Kober et al.

(10) Patent No.: US 8,497,230 B2
(45) Date of Patent: Jul. 30, 2013

(54) SOLID CROP PROTECTION AGENTS CONTAINING POLYALKOXYLATE, METHOD FOR THEIR PRODUCTION AND USE THEREOF

(75) Inventors: Reiner Kober, Fußgöheim (DE); Reinhold Stadler, Kirrweiler (DE); Karl-Otto Westphalen, Speyer (DE); Thomas Christen, Dannstadt (DE); Michael Krapp, Altrip (DE); Karl-Friedrich Jaeger, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1428 days.

(21) Appl. No.: 12/084,233

(22) PCT Filed: Oct. 27, 2006

(86) PCT No.: PCT/EP2006/067899
§ 371 (c)(1),
(2), (4) Date: Apr. 28, 2008

(87) PCT Pub. No.: WO2007/048851
PCT Pub. Date: May 3, 2007

(65) Prior Publication Data
US 2009/0170704 A1 Jul. 2, 2009

(30) Foreign Application Priority Data
Oct. 28, 2005 (DE) .......................... 10 2005 051 823

(51) Int. Cl.
*A01N 25/10* (2006.01)
(52) U.S. Cl.
USPC ........................................................ 504/360
(58) Field of Classification Search
None
See application file for complete search history.

(56) References Cited

U.S. PATENT DOCUMENTS

| | | | |
|---|---|---|---|
| 5,730,996 A * | 3/1998 | Beall et al. | ..................... 424/405 |
| 6,239,115 B1 | 5/2001 | Tokumura et al. | |
| 6,375,969 B1 | 4/2002 | Kostka et al. | |
| 6,416,775 B1 | 7/2002 | Kostka et al. | |
| 2005/0100562 A1 * | 5/2005 | Kurita et al. | ................. 424/400 |

FOREIGN PATENT DOCUMENTS

| | | |
|---|---|---|
| DE | 696 24 381 T2 | 12/1998 |
| DE | 102 17 201 A1 | 7/2003 |
| EP | 0 707 445 B1 | 4/1996 |
| EP | 0 843 964 B1 | 5/1998 |
| EP | 0 880 402 B1 | 12/1998 |
| GB | 1291251 | 10/1972 |
| WO | WO-93/05652 A1 | 4/1993 |
| WO | WO-93/25074 A1 | 12/1993 |
| WO | WO 9325074 A1 * | 12/1993 |
| WO | WO9325074 A3 * | 12/1993 |
| WO | WO-95/18531 A1 | 7/1995 |
| WO | WO 9518531 A1 * | 7/1995 |
| WO | WO-97/24173 A1 | 7/1997 |
| WO | WO-98/12920 A1 | 4/1998 |
| WO | WO 9812920 A1 * | 4/1998 |
| WO | WO-99/08518 A1 | 2/1999 |
| WO | WO-99/56543 A1 | 11/1999 |
| WO | WO-03/055959 A1 | 7/2003 |

* cited by examiner

*Primary Examiner* — James H Alstrum Acevedo
*Assistant Examiner* — Thor Nielsen
(74) *Attorney, Agent, or Firm* — Birch, Stewart, Kolasch & Birch, LLP

(57) ABSTRACT

The invention relates to solid plant protection compositions comprising:
  a) liquid or low melting point polyalkoxylate; and
  b) a carrier based on relatively high molecular weight sulfonate,
  wherein
    (i) the weight ratio of liquid or low melting point polyalkoxylate to plant protection active agent is at least 1:2;
    (ii) the proportion of liquid or low melting point polyalkoxylate, based on the total weight of the relatively high molecular weight sulfonates, is at least 30% by weight; and
    (iii) the weight ratio of liquid or low melting point polyalkoxylate to relatively high molecular weight sulfonate is at most 3:1.

The invention also relates to processes for their preparation and the use of the plant protection compositions for the treatment of plants and their habitat as well as corresponding processes, and also spray mixtures comprising such a plant protection composition.

49 Claims, 1 Drawing Sheet

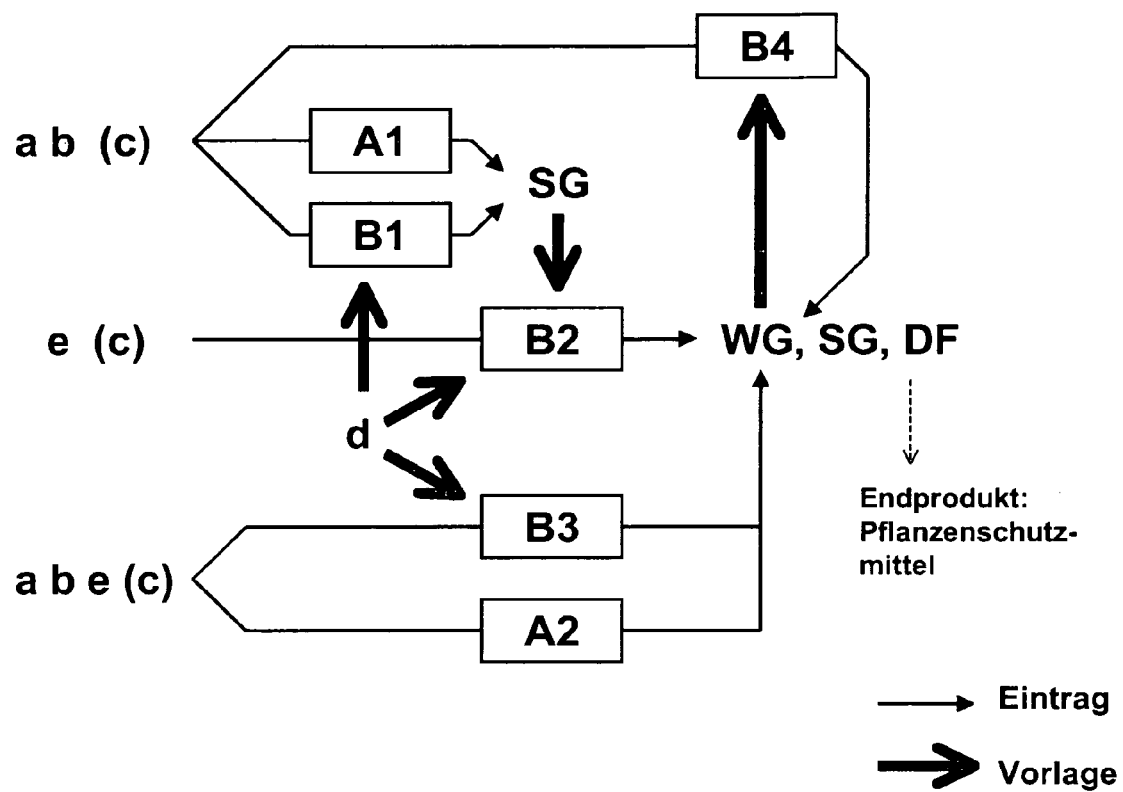

SOLID CROP PROTECTION AGENTS CONTAINING POLYALKOXYLATE, METHOD FOR THEIR PRODUCTION AND USE THEREOF

The invention relates to solid plant protection compositions with liquid or low melting point polyalkoxylates, processes for their preparation and the use of the plant protection compositions for the treatment of plants and their habitat as well as corresponding processes, and also spray mixtures comprising such a plant protection composition.

Year in, year out, worldwide, a considerable portion of agricultural production is destroyed by plant pests in the broadest sense. Plant pests can not only lead to crop failure on a large scale, which threatens human alimentation, but also destroy the vegetative parts of useful perennial plants and thereby impair agriculturally productive land and whole ecosystems with lasting effect.

Plant pests belong to different groups of organisms. Numerous important pests are to be found among higher animals, in particular among insects and acarids, and furthermore among nematodes and snails; vertebrates, such as mammals and birds, are today of lesser importance in industrialized countries. Numerous groups of microbes, including fungi, bacteria inclusive of mycoplasmas, viruses and viroids, can cause crop failure and loss of value; even products still essentially edible are often no longer marketable for aesthetic reasons. Finally, weeds which compete with useful plants for limited living space and other resources also belong to pests in the broad sense.

Parasitic fungi are particularly important as pests. Mildew is to be feared in horticulture, ergot (Claviceps) is a danger to man and animals due to its toxic alkaloids, and the damage to European potato stocks by *Phytophthora infestans* in the middle of the 19th century, which led to famine and political unrest, achieved historical importance.

The generic term "plant protection compositions" brings together substances and mixtures of substances which can be used for specific control of plant pests. They can be classified according to target organisms (insecticides, fungicides, herbicides, and the like), according to manner of action (stomach poison, contact poisons, repellents, and the like) or according to chemical structure. Due to the resistance of fungal spores and the lack of natural enemies, chemical control is the only effective measure in particular against phytotoxic fungi, care having to be taken to locally maximize the effect of the fungicides in order not to damage symbiotic fungi (mycorrhizal fungi) in other places.

Plant protection compositions can be pure substances; however, compositions are in many cases advantageous. Such compositions can, in addition to the substance or substances having an immediate effect on the pests (subsequently denoted as plant protection active agent), comprise various types of accompanying and auxiliary substances which in various ways can strengthen the desired effect (in the literature then generally known as "additives", "adjuvants", "accelerators", "boosters" or "enhancers"), simplify the handling, increase the shelf life or otherwise improve the properties of the product. Subsequently, a plant protection composition always describes a combination of one or more plant protection active agents and one or more auxiliaries.

Typically, plant protection compositions are dissolved, emulsified or dispersed in aqueous medium in order thus to obtain the aqueous spray mixture described as "tank mix" which is then applied in the "spray method" to the plants or their habitat. The accompanying and auxiliary substances must be appropriately chosen in order to obtain a suitable tank mix.

The action of the effect-promoting additives is generally based on their surface activity with regard to the hydrophobic plant surface, which improves the contact of the spray mixture with the plant surface. A distinction is made in detail between wetters, spreaders and penetrators, these groups naturally overlapping. Subsequently, the general term "additive" is used without consideration of physical details to describe auxiliaries for enhancing the effect of agrotechnical active agents, in particular plant protection agents.

Nonionic hydrophobic alkoxylates are known as suitable additives for various plant protection active agents, in particular fungicides.

Such alkoxylates are above all used in liquid formulations, including solutions, emulsions, suspensions, suspoemulsions and other forms. For example, relatively stable suspoemulsions are represented in EP 707 445 B1.

However, liquid plant protection compositions exhibit a number of disadvantages: on application, the danger arises of runoff and seepage into the soil. Storage and transportation are more expensive since the solvent has to be transported or stored too and receptacles for liquid plant protection compositions, for example containers or cans, cause waste disposal problems since simple incineration is generally impossible. The stability of liquid plant protection compositions with regard to heat, cold and shear forces and accordingly their storage stability is low and requires expensive emulsifying and stabilizing additives. Moreover, many active agents or active agent combinations can only with difficulty be formulated in liquid form since they are prone to crystallization and/or demixing. The solvents as such are often readily flammable, are skin irritating or have an unpleasant smell; if water is used as solvent, the problem of hydrolytic decomposition of active agent frequently occurs during prolonged storage.

Solid plant protection compositions, in particular those based on dust-free solid granules, offer considerable advantages in comparison with liquid plant protection compositions, which affects use, storage, transportation, stability and waste disposal of packaging materials. However, the low melting point of the abovementioned alkoxylates, which leads to problems on incorporation in solid plant protection compositions, is frequently disadvantageous. Thus, conventional solid plant protection compositions can only include small amounts of liquid, oily or low melting point additives, such as those represented by the alkoxylates, since otherwise agglutination and aggregation of the granules occur. Typically, less than 15% by weight merely of such additives can be added without harming the storage stability.

The usable proportion of additives can conventionally be increased by use of sorbent materials, also known as carriers, based on inorganic compounds, especially based on silicate. By binding the additives, they improve the mechanical properties of the composition and prevent aggregation of the granules during storage. However, inorganic sorbent materials have a tendency to form very fine-grained powders and dusts, which again raises problems in the preparation and processing and in particular necessitates expensive safety engineering, especially in the area of respiratory protection. The health hazard from fine-grained inorganic dusts is known. In addition, the solid constituents can also exhibit undesirable effects after application.

U.S. Pat. No. 6,239,115 B1 discloses granules with the active agent polyoxin and naphthalenesulfonic acid-formaldehyde condensates as dispersant. Typically, however, only 2% of polyoxyethylene alkyl ethers were incorporated in the granules here.

DE 102 17 201 discloses low-dust granules with up to 9% of alkylsulfonates and/or polyglycols. The polyglycols are generally not suitable enhancers of activity since they are purely water-soluble and are not surface-active.

GB 1 291 251 discloses granules with merely up to 5% of anionic and nonionic surfactants but up to 50% of calcium lignosulfonates.

The incorporation of surface-active and activity-enhancing auxiliaries can, e.g., also be carried out via melt extrudates (melt extrusion process). Examples thereof are found in WO 93/25074, where virtually without exception carbowax (PEG 8000) is used as "binder". PEGs, i.e. polyethylene glycols, are generally very hydrophilic and thus very highly soluble in water.

EP 843 964 B1 discloses essentially extrusion granules with up to 10% of tristyryl-phenyl polyethoxylates, inorganic carrier systems as in U.S. Pat. No. 6,416,775 B1 being used. Thus, diatomaceous earths (kieselguhr), in particular Celite products, are used in U.S. Pat. No. 6,416,775 B1 or in U.S. Pat. No. 6,375,969 B1 as sorbent agents.

Granules made of lignosulfonates with relatively low proportions of di- and tristyrylphenol ethoxylates are disclosed in DE 696 24 381 T2, WO 97/24173 or EP 880 402 B1.

A route to the preparation of granules with high contents of liquid amphiphilic surface-active additives is disclosed, e.g., in WO 99/56543 and WO 99/08518. "Clathrates" formed from urea derivatives and polysiloxane-derived alcohol ethoxylates are disclosed here. It is stated that powders or granules with up to 30% of surface-active auxiliaries can be prepared.

A solution for the preparation of herbicidal granules with "active agents" is demonstrated in WO 93/05652. If fatty alcohol ethoxylates are used, high proportions of inorganic sorbent materials or carriers based on silicate occur in the granules. These sorbent materials or carriers have the disadvantages demonstrated above.

In summary, it can be said that the state of the art demonstrates no way of incorporating high proportions of liquid or low melting point additives in solid formulations without having to fall back on inorganic carrier systems. For this reason, the object was to provide solid plant protection compositions with high proportions of such additives.

Surprisingly, it has now been found that liquid or low melting point polyalkoxylates, combined in suitable amounts with relatively high molecular weight sulfonates, are able to provide advantageous solid plant protection compositions, in particular granules.

An object of the present invention is accordingly a solid plant protection composition comprising a plant protection active agent which comprises:
a) liquid or low melting point polyalkoxylate; and
b) a carrier based on relatively high molecular weight sulfonate,
wherein
  (i) the weight ratio of liquid or low melting point polyalkoxylate to plant protection active agent is at least 1:2;
  (ii) the proportion of liquid or low melting point polyalkoxylate, based on the total weight of the relatively high molecular weight sulfonate, is at least 30% by weight; and
  (iii) the weight ratio of liquid or low melting point polyalkoxylate to relatively high molecular weight sulfonate is at most 3:1.

The plant protection composition according to the invention accordingly comprises, in addition to the active agent (component (e)), basically two components:
(a) a polyalkoxylate component which, taken by itself, is liquid or has a low melting point and consists of a polyalkoxylate or a mixture of several polyalkoxylates; and
(b) a carrier component which, taken by itself, is solid and which comprises one or more relatively high molecular weight sulfonates.

In this context, the proportion of liquid or low melting point polyalkoxylate, based on the amount of active agent, is at least 0.5, preferably at least 1 and in particular at least 2. According to an additional aspect, the proportion of liquid or low melting point polyalkoxylate is at least 15% by weight, based on the total weight of the composition, and at least 30%, based on the total weight of the relatively high molecular weight sulfonates. In this context, the proportion of liquid or low melting point polyalkoxylates can even be greater than the proportion of relatively high molecular weight sulfonate, at most, however, up to a weight ratio of 3:1. The carrier component (b) generally for the most part comprises relatively high molecular weight sulfonate.

The term "liquid" describes the liquid physical state at standard pressure and a temperature in the range from 20 to 30° C. A low melting point polyalkoxylate generally has a melting point of less than 40° C., in particular of less than 30° C.

According to a particular embodiment, the polyalkoxylate to be used is oily. In this context, the term "oily" describes a viscous sticky-greasy physical consistency; chemically, the substance can be looked at as lipophilic, hydrophilic or amphiphilic. The polyalkoxylates are generally amphiphilic.

The polyalkoxylates according to the invention basically comprise a hydrophobic or lipophilic portion and one or more polymeric alkoxylate portions (polyalkoxylate or macrogol portions), the polyalkoxylate portion or each individual polyalkoxylate portion being coupled, for example via an amide, ether or ester bond, to the hydrophobic or lipophilic portion. The term "polymer" means in this context put together from at least two, in particular at least three, very particularly from 3 to 1000, low molecular weight units. These units can either be all of the same kind, so that a monotonic polymer is formed, or can comprise at least two different types of alkylene oxide. In the latter case, it is preferable each time to arrange several alkylene oxide units of one type as a block, so that at least two different alkylene oxide blocks ensue as structural elements of the polymer, each of which consists of a monotonic sequence of identical alkylene oxide units (block polymer or block copolymer). If such block alkoxylates are used, it is preferable for the alkylene oxide portion to be composed of 2 or 3 and in particular of 2 blocks. If the polyalkoxylate portion comprises different blocks, those lying closer to the hydrophobic or lipophilic portion are described as "proximal", those lying further away are described as "distal" and those positioned at the end are described as "terminal". Mention may in particular be made here, as alkoxylate monomers according to the invention, of ethylene oxide (EO), propylene oxide (PO), butylene oxide (BO), pentylene oxide (PeO) and hexylene oxide (HO).

Particular polyalkoxylates are found among alkoxylated fatty alcohols, alkoxylated fatty acid esters, alkoxylated fatty amines, alkoxylated glycerides, alkoxylated sorbitan esters, alkoxylated alkylphenols and alkoxylated di- and tristyrylphenols, the alkylphenols preferably being polyalkylated, in particular dialkylated or trialkylated. Furthermore, the polyalkoxylates can also be end-group-modified, i.e. the terminal OH group of the alkoxylate portion is modified, for example etherified or esterified. Suitable end-group-modified polyalkoxylates include in particular alkylated, alkenylated or arylated polyalkoxylates, preferably those with a methyl or tert-butyl group or a phenyl group, or polyalkoxylate esters, e.g. mono- or diphosphate esters or sulfate esters, and their salts, for example the alkali metal or alkaline earth metal salts. Such an end-group modification can, for example, be carried out with dialkyl sulfate, $C_{1-10}$-alkyl halide or phenyl halide.

At least some of the alcohol polyalkoxylates to be used are known per se. For example, WO 01/77276 and U.S. Pat. No. 6,057,284 or EP 0 906 150 disclose suitable alcohol polyalkoxylates. Reference is expressly made herewith to the description of these alcohol polyalkoxylates in these documents, by which the alcohol polyalkoxylates themselves and also their preparation disclosed therein are part of the present disclosure.

In an additional particular embodiment, alcohol polyalkoxylates are chosen from alcohol polyalkoxylates according to the formula (I)

$$R^7\text{—}O\text{—}(C_mH_{2m}O)_x\text{—}(C_nH_{2n}O)_y\text{—}(C_pH_{2p}O)_z\text{—}R^6 \qquad (I)$$

in which
$R^6$ is an organic radical;
$R^7$ is an aliphatic hydrocarbon radical with from 3 to 100 carbon atoms;
m, n and p are, independently of one another, a whole number from 2 to 6, preferably 2, 3, 4 or 5;
x, y and z are, independently of one another, a number from 0 to 1000; and
x+y+z corresponds to a value from 2 to 1000.

The aliphatic hydrocarbon radical is generally hydrophobic or lipophilic, by which the alcohol polyalkoxylates obtain their oily properties. In particular, $R^1$ is a branched or linear hydrocarbon radical with from 3 to 30 and preferably from 5 to 24 carbon atoms which can be saturated (in particular $C_{3-30}$-alkyl) or unsaturated (in particular $C_{3-30}$-alkenyl).

The organic radical ($R^6$) typically contributes less than 10% and preferably less than 5% to the molecular weight of the alcohol polyalkoxylate of the formula (I) and is preferably hydrogen, alkyl, preferably $C_{1-10}$-alkyl, particularly preferably methyl or tert-butyl, alkenyl, preferably $C_{2-10}$-alkenyl, acyl, in particular acetyl, propionyl, butyryl or benzoyl, or aryl, in particular phenyl, or is an inorganic acid group, in particular phosphate, diphosphate or sulfate.

According to one aspect, it is preferable for the alcohol polyalkoxylates to be used according to the invention to be ethoxylated or to exhibit at least one ethylene oxide block. According to an additional aspect, ethylene oxide blocks are combined in particular with propylene oxide or pentylene oxide blocks.

According to a particular embodiment, use is made of alcohol polyalkoxylates of the formula (I) in which m=2 and x>0. In this context, alcohol polyalkoxylates of EO type are concerned, including above all alcohol ethoxylates (m=2; x>0; y, z=0) and alcohol polyalkoxylates with a proximal EO block (m=2; x>0; y and/or z>0).

Again, a particular embodiment of the alcohol polyalkoxylates with a proximal EO block is represented by those with a terminal block made from other monomers (n>2; y>0). Mention may be made, among these, above all of EO-PO block alkoxylates (n=3; y>0; z=0). Preference is given to EO-PO block alkoxylates in which the ratio of EO to PO (x to y) is preferably from 1:1 to 4:1 and in particular from 1.5:1 to 3:1. In this context, the degree of ethoxylation (value of x) is generally from 1 to 20, preferably from 2 to 15 and in particular from 4 to 10 and the degree of propoxylation (value of y) is generally from 1 to 20, preferably from 1 to 8 and in particular from 2 to 5. The total degree of alkoxylation, i.e. the sum of EO and PO units, is generally from 2 to 40, preferably from 3 to 25 and in particular from 6 to 15.

Mention may also be made, among the particularly preferred alcohol polyalkoxylates with a proximal EO block, of EO-PeO block alkoxylates (n=5; y>0; z=0). Preference is given in this context to EO-PeO block alkoxylates in which the ratio of EO to PeO (x to y) is preferably from 2:1 to 25:1 and in particular from 4:1 to 15:1. In this context, the degree of ethoxylation (value of x) is generally from 1 to 50, preferably from 4 to 25 and in particular from 6 to 15 and the degree of pentoxylation (value of y) is generally from 0.5 to 20, preferably from 0.5 to 40 and in particular from 0.5 to 2. The total degree of alkoxylation, i.e. the sum of EO and PeO units, is generally from 1.5 to 70, preferably from 4.5 to 29 and in particular from 6.5 to 17.

According to an additional particular embodiment, use is made of alcohol polyalkoxylates of the formula (I) in which n=2, the values of m, x and y are each time greater than zero and z=0. In this context, alcohol polyalkoxylates of EO type are also concerned in which the EO block is, though, distally bonded and an additional polyalkoxylate block is inserted between it and the alkyl part. These include above all PO-EO block alkoxylates and PeO-EO block alkoxylates (n=2; x>0; y>0; m=5; z=0).

Again, a particular embodiment of such alcohol polyalkoxylates with distal EO block is represented by PO-EO block alkoxylates (n=2; x>0; y>0; m=3; z=0), in which the ratio of PO to EO (x to y) is preferably from 1:10 to 3:1 and in particular from 1.5:1 to 1:6. In this context, the degree of ethoxylation (value of y) is generally from 1 to 20, preferably from 2 to 15 and in particular from 4 to 10 and the degree of propoxylation (value of x) is generally from 0.5 to 10, preferably from 0.5 to 6 and in particular from 1 to 4. The total degree of alkoxylation, i.e. the sum of EO and PO units, is generally from 1.5 to 30, preferably from 2.5 to 21 and in particular from 5 to 14.

According to another particular embodiment, use is made of alcohol polyalkoxylates of the formula (I) in which m=5 and x>0. In this context, alcohol polyalkoxylates of PeO type are concerned. Particular preference is given in this context to PeO-EO block alkoxylates (n=2; y>0; z=0), in which the ratio of PeO to EO (x to y) is from 1:50 to 1:3 and in particular from 1:25 to 1:5. In this context, the degree of pentoxylation (value of x) is generally from 0.5 to 20, preferably from 0.5 to 4 and in particular from 0.5 to 2 and the degree of ethoxylation (value of y) is generally from 3 to 50, preferably from 4 to 25 and in particular from 5 to 15. The total degree of alkoxylation, i.e. the sum of EO and PeO units, is generally from 3.5 to 70, preferably from 4.5 to 45 and in particular from 5.5 to 17.

According to a particular embodiment, the alcohol polyalkoxylates are not end-group-modified, i.e. $R^6$ is hydrogen.

According to a preferred embodiment of the invention, the alcohol portion of the alcohol polyalkoxylates is based on alcohols or mixtures of alcohols known per se with from 5 to 30, preferably from 8 to 20 and in particular from 9 to 15 carbon atoms. Mention may be made here in particular of fatty alcohols with from approximately 8 to 20 carbon atoms. Many of these fatty alcohols are, as is known, used for the preparation of nonionic and anionic surfactants, for which the alcohols are subjected to an appropriate functionalization, e.g. by alkoxylation or glycosidation.

The alcohol portion can be straight-chain, branched or cyclic. If it is linear, mention may thus in particular be made of alcohols with from 14 to 20, for example with from 16 to 18, carbon atoms. If it is branched, the main chain of the alcohol portion generally exhibits, according to a particular embodiment, from 1 to 4 branchings, it also being possible for alcohols with higher or lower degrees of branching to be used in combination with additional alcohol alkoxylates, provided that the average number of the branchings of the mixture lies in the given range.

The alcohol portion can be saturated or unsaturated. If it is unsaturated, it thus exhibits, according to a particular embodiment, a double bond. Generally, the branchings of the alcohol portion exhibit, independently of one another, each time from 1 to 10, preferably from 1 to 6 and in particular from 1 to 4 carbon atoms. Particular branchings are methyl, ethyl, n-propyl or isopropyl groups.

Suitable alcohols and in particular fatty alcohols can be obtained both from native sources, e.g. by extraction, and optionally, as necessary, by hydrolysis, transesterification and/or hydrogenation of glycerides and fatty acids, and synthetically, e.g. by synthesis from educts with a lower number of carbon atoms. Thus, e.g., olefin fractions with a carbon number suitable for further processing to give surfactants are obtained, starting from ethers, according to the SHOP (Shell Higher Olefine Process) process. The functionalization of the olefins to give the corresponding alcohols is carried out in this context, e.g. by hydroformylation and hydrogenation.

The alkoxylation results from the reaction with suitable alkylene oxides. The prevailing degree of alkoxylation depends on the dosages of alkylene oxide(s) chosen for the reaction and on the reaction conditions. In this context, a statistical mean value is generally concerned since the number of alkylene oxide units of the alcohol polyalkoxylates resulting from the reaction varies.

The degree of alkoxylation, i.e. the mean chain length of the polyether chains of the alcohol polyalkoxylates to be used according to the invention, can be determined by the molar ratio of alcohol to alkylene oxide. Preference is given to alcohol polyalkoxylates with from approximately 2 to 100, preferably from approximately 2 to 50, in particular from 3 to 30, above all from 4 to 20 and especially from 5 to 15 alkylene oxide units.

The reaction of the alcohols or alcohol mixtures with the alkylene oxide(s) is carried out according to conventional processes known to a person skilled in the art and using conventional equipment therefor.

The alkoxylation reaction can be catalyzed by strong bases, such as alkali metal hydroxides and alkaline earth metal hydroxides, Brönsted acids or Lewis acids, such as $AlCl_3$, $BF_3$, and the like. Catalysts such as hydrotalcite or DMC can be used for narrowly distributed alcohol alkoxylates.

The alkoxylation is preferably carried out at temperatures ranging from approximately 80 to 250° C., preferably from approximately 100 to 220° C. The pressure is preferably between ambient pressure and 600 bar. If desired, the alkylene oxide can comprise an inert gas admixture, e.g. from approximately 5 to 60%.

According to a preferred embodiment, the alcohol polyalkoxylates to be used according to the invention are based on primary, α-branched alcohols of the formula (IV):

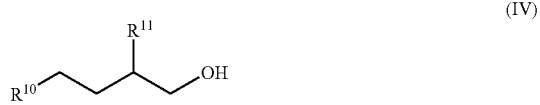

(IV)

in which
$R^{10}$ and $R^{11}$ are, independently of one another, hydrogen or $C_1$-$C_{26}$-alkyl.

Preferably, $R^{10}$ and $R^{11}$ are, independently of one another, $C_1$-$C_6$-alkyl and in particular $C_2$-$C_4$-alkyl.

According to a particular embodiment, use is made of alcohol polyalkoxylates in which 2-propylheptanol is the alcohol portion. These include in particular alcohol polyalkoxylates of the formula (I) in which $R^7$ is a 2-propylheptyl radical, i.e. each of $R^{10}$ and $R^{11}$ in formula (IV) represent n-propyl.

Such alcohols are also described as Guerbet alcohols. These can, for example, be obtained by dimerization of the corresponding primary alcohols (e.g. $R^{10,11}$—$CH_2CH_2OH$) at elevated temperature, for example from 180 to 300° C., in the presence of an alkaline condensation catalyst, such as potassium hydroxide. Within the framework of this preferred embodiment based on Guebert alcohols, use is made in particular of alkoxylates of EO type. Ethoxylates having a degree of ethoxylation of from 2 to 50, preferably from 2 to 20 and in particular from approximately 3 to 10 are particularly preferred. Mention may expressly be made, among these, of the appropriately ethoxylated 2-propylheptanols.

According to an additional particular embodiment, use is made of alcohol polyalkoxylates in which the alcohol portion is a $C_{13}$-oxo alcohol.

It is particularly preferred for these $C_{13}$-oxo alcohols to be obtained by hydroformylation and subsequent hydrogenation of unsaturated $C_{12}$-hydrocarbons, in particular by hydrogenation of hydroformylated trimeric butene or by hydrogenation of hydroformylated dimeric hexene.

The term "$C_{13}$-oxo alcohol" generally describes an alcohol mixture, the main component of which is formed from at least one $C_{13}$-alcohol (isotridecanol). Such $C_{13}$-alcohols include in particular tetramethylnonanols, for example 2,4,6,8-tetramethyl-1-nonanol or 3,4,6,8-tetramethyl-1-nonanol, and furthermore ethyldimethylnonanols, such as 5-ethyl-4,7-dimethyl-1-nonanol.

Suitable $C_{13}$-alcohol mixtures can generally be obtained by hydrogenation of hydroformylated trimeric butene. In particular, it is possible
1) to bring butenes, for oligomerization, into contact with a suitable catalyst,
2) to isolate a $C_{12}$-olefin fraction from the reaction mixture,
3) to hydroformylate the $C_{12}$-olefin fraction by reaction with carbon monoxide and hydrogen in the presence of a suitable catalyst, and
4) to hydrogenate.

The butene trimerization preceding the hydrogenation can be carried out using homogeneous or heterogeneous catalysis.

A $C_{12}$-olefin fraction is first isolated in one or more separation stages from the reaction product of the oligomerization reaction described, which fraction is then suitable for the preparation, by hydroformylation and hydrogenation, of usable $C_{13}$-alcohol mixtures (process stage 2). The conventional devices known to a person skilled in the art are suitable separating devices.

The $C_{12}$-olefin fraction thus isolated is hydroformylated to give $C_{13}$-aldehydes (process stage 3) and subsequently hydrogenated to give $C_{13}$-alcohols (process stage 4) for the preparation of an alcohol mixture according to the invention. In this context, the alcohol mixtures can be prepared in one stage or in two separate reaction stages.

A review of hydroformylation processes and suitable catalysts appears in Beller et al., Journal of Molecular Catalysis A, 104 (1995), pp. 17-85.

For the hydrogenation, the reaction mixtures obtained in the hydroformylation are reacted with hydrogen in the presence of a hydrogenation catalyst.

Additional suitable $C_{13}$-alcohol mixtures can be obtained by
1) subjecting a $C_4$-olefin mixture to metathesis,
2) separating olefins with 6 carbon atoms from the metathesis mixture,
3) subjecting the separated olefins, individually or in the mixture, to a dimerization to give olefin mixtures with 12 carbon atoms, and
4) subjecting the olefin mixture thus obtained, optionally after a fractionation, to the derivatization to give a mixture of $C_{13}$-oxo alcohols.

The $C_{13}$-alcohol mixture according to the invention can be obtained pure for use as component (a) from the mixture obtained after the hydrogenation according to conventional purification processes known to a person skilled in the art, in particular by fractional distillation.

$C_{13}$-alcohol mixtures according to the invention generally exhibit a mean degree of branching of from 1 to 4, preferably from 2.0 to 2.5 and in particular from 2.1 to 2.3 (based on trimeric butene) or from 1.3 to 1.8 and in particular from 1.4 to 1.6 (based on dimeric hexene). The degree of branching is defined as number of the methyl groups in a molecule of the alcohol minus 1. The mean degree of branching is the statistical mean value of the degrees of branching of the molecules of a sample. The mean number of the methyl groups in the molecules of a sample can be readily determined by $^1$H NMR spectroscopy. For this, the signal area corresponding to the methyl protons in the $^1$H NMR spectrum of a sample is divided by 3 and compared with the signal area, divided by 2, of the methylene protons in the $CH_2$—OH group.

Within the framework of this particular embodiment based on $C_{13}$-oxo alcohols, preference is given in particular to those alcohol alkoxylates which are either ethoxylated or are block alkoxylates of EO/PO type.

The degree of ethoxylation of the ethoxylated $C_{13}$-oxo alcohols to be used according to the invention is generally from 1 to 50, preferably from 3 to 20 and in particular from 3 to 10, especially from 4 to 10 and particularly from 5 to 10.

The degrees of alkoxylation of the EO/PO block alkoxylates to be used according to the invention depend on the arrangement of the blocks. If the PO blocks are terminally arranged, the ratio of EO units to PO units is thus generally at least 1, preferably from 1:1 to 4:1 and in particular from 1.5:1 to 3:1. In this context, the degree of ethoxylation is generally from 1 to 20, preferably from 2 to 15 and in particular from 4 to 10 and the degree of propoxylation is generally from 1 to 20, preferably from 1 to 8 and in particular from 2 to 5. The total degree of alkoxylation, i.e. the sum of EO and PO units, is generally from 2 to 40, preferably from 3 to 25 and in particular from 6 to 15. On the other hand, if the EO blocks are terminally arranged, the ratio of PO blocks to EO blocks is less critical and is generally from 1:10 to 3:1, preferably from 1:1.5 to 1:6. In this context, the degree of ethoxylation is generally from 1 to 20, preferably from 2 to 15 and in particular from 4 to 10 and the degree of propoxylation is generally from 0.5 to 10, preferably from 0.5 to 6 and in particular from 1 to 4. The total degree of alkoxylation is generally from 1.5 to 30, preferably from 2.5 to 21 and in particular from 5 to 14.

According to an additional particular embodiment, use is made of alcohol polyalkoxylates in which the alcohol portion is a $C_{10}$-oxo alcohol. The term "$C_{10}$-oxo alcohol" represents, analogously to the term "$C_{13}$-oxo alcohol" already explained, $C_{10}$-alcohol mixtures having a main component formed from at least one branched $C_{10}$-alcohol (isodecanol).

It is particularly preferable for suitable $C_{10}$-alcohol mixtures to be obtained by hydrogenation of hydroformylated trimeric propene.

In particular, it is possible
1) to bring propenes into contact with a suitable catalyst for the purpose of oligomerization,
2) to isolate a $C_9$-olefin fraction from the reaction mixture,
3) to hydroformylate the $C_9$-olefin fraction by reaction with carbon monoxide and hydrogen in the presence of a suitable catalyst, and
4) to hydrogenate.

Particular embodiments of this procedure ensue by analogy to the embodiments described above for the hydrogenation of hydroformylated trimeric butene.

Within the framework of this particular embodiment based on $C_{10}$-oxo alcohols, preference is given in particular to those alcohol alkoxylates which are either ethoxylated or are block alkoxylates of EO/PeO type.

The degree of ethoxylation of the ethoxylated $C_{10}$-oxo alcohols to be used according to the invention is generally from 2 to 50, preferably from 2 to 20 and in particular from 2 to 10, especially from 3 to 10 and particularly from 3 to 10.

The degrees of alkoxylation of the EO/PeO block alkoxylates to be used according to the invention depend on the arrangement of the blocks. If the PeO blocks are terminally arranged, the ratio of EO units to PeO units is thus generally at least 1, preferably from 2:1 to 25:1 and in particular from 4:1 to 15:1. In this context, the degree of ethoxylation is generally from 1 to 50, preferably from 4 to 25 and in particular from 6 to 15 and the degree of pentoxylation is generally from 0.5 to 20, preferably from 0.5 to 4 and in particular from 0.5 to 2. The total degree of alkoxylation, i.e. the sum of EO and PeO units, is generally from 1.5 to 70, preferably from 4.5 to 29 and in particular from 6.5 to 17. On the other hand, if the EO blocks are terminally arranged, the ratio of PeO blocks to EO blocks is less critical and is generally from 1:50 to 1:3, preferably from 1:25 to 1:5. In this context, the degree of ethoxylation is generally from 3 to 50, preferably from 4 to 25 and in particular from 5 to 15 and the degree of pentoxylation is generally from 0.5 to 20, preferably from 0.5 to 4 and in particular from 0.5 to 2. The total degree of alkoxylation is generally from 3.5 to 70, preferably from 4.5 to 45 and in particular from 5.5 to 17.

It follows, from the above embodiments, that in particular the $C_{13}$-oxo alcohols or $C_{10}$-oxo alcohols to be used according to the invention are based on olefins which are already branched. In other words, branchings are not only to be traced back to the hydroformylation reaction, as would be the case in the hydroformylation of straight chain olefins. Consequently, the degree of branching of the alkoxylates to be used according to the invention is generally greater than 1.

The alkoxylates to be used according to the invention generally exhibit a relatively low contact angle. Particular preference is given to alkoxylates having a contact angle of less than 120° and preferably of less than 100° when this is determined in a way known per se on a paraffin surface for an aqueous solution comprising 2% by weight of alkoxylate.

According to one aspect, the surface-active properties of the polyalkoxylates depend on the type and distribution of the polyalkoxylate grouping. The surface tension of the polyalkoxylates to be used according to the invention, which can be determined according to the pendant drop method, preferably ranges from 25 to 70 mN/m and in particular from 28 to 50 mN/m for a solution comprising 0.1% by weight of polyalkoxylate and ranges from 25 to 70 mN/m and in particular from 28 to 45 mN/m for a solution comprising 0.5% by weight of polyalkoxylate. Polyalkoxylates preferably to be used according to the invention accordingly qualify as amphiphilic substances.

Typical commercial products of the formula (I) are familiar to a person skilled in the art. They are, e.g., offered for sale by BASF under the general brand name of the "Lutensoles", Lutensoles of the series A, AO, AT, ON, AP and FA being differentiated according to the base alcohol. Furthermore, included numbers give the degree of ethoxylation. Thus, e.g., "Lutensol AO 8" is a $C_{13-15}$-oxo alcohol with eight EO units. "Lutensol ED" represents a series of alkoxylated amines.

Additional examples of polyalkoxylates according to the invention are products from Akzo, e.g. the "Ethylan" series based on linear or branched alcohols. Thus, e.g., "Ethylan SN 120" is a $C_{10-12}$-alcohol with ten EO units and "Ethylan 4 S" is a $C_{12-14}$-alcohol with four EO units.

Additional examples of polyalkoxylates according to the invention are furthermore the "NP" products from Akzo (formerly Witco) based on nonylphenols. Nonylphenol alkoxylates or analogous monoalkylphenol alkoxylates and their derivatives are not preferred for use in Europe since European approving authorities are assessing them very critically with regard to their potential endocrinal effects. With regard to this, di- or polyalkyl-substituted aryl or polyaryl alkoxylates, which are not criticized, are preferred for Europe.

Additional examples of polyalkoxylates according to the invention are castor oil ethoxylates (castor oil-$EO_x$), e.g. products of the "Emulphon CO" or "Emulphon EL" product series from Akzo, such as, for example, "Emulphon CO 150" with 15 EO units, or products of the "Ethomee" series based on coconut oil amines or tallow oil amines, e.g. "Ethomee C/25", a coconut oil amine with 25 EO units.

Alkoxylates according to the invention also comprise "narrow range" products. The expression "narrow range" refers in this context to a fairly narrow distribution in the number of the EO units. These include, e.g., products of the "Berol" series from Akzo.

Furthermore, sorbitan ester ethoxylates, e.g. "Armotan AL 69-66 POE(30) sorbitan monotallate", thus an unsaturated fatty acid esterified with sorbitol and subsequently ethoxylated, are according to the invention.

Mixtures of different polyalkoxylates can also be used as component (a).

According to a particular embodiment of the invention, the composition comprises at least 20% by weight, preferably at least 25% by weight and in particular at least 30% by weight of alkoxylate.

According to an additional particular embodiment of the invention, the composition comprises at most 70% by weight, preferably at most 60% by weight and in particular at most 45% by weight of alkoxylate.

Use may generally be made, as carrier component (b), of solid, relatively high molecular weight, for example polymeric or macromolecular, organic sulfonates. The term "sulfonate" here represents a salt which is composed of sulfonate anions and suitable cations.

In this context, it is particularly preferable for the relatively high molecular weight sulfonate to be soluble in water. The sulfonates according to the invention, in contrast to typical carriers, which are generally based on water-insoluble inorganic solids, can accordingly be introduced in dissolved form, preferably as aqueous concentrates, in the preparation of the solid plant protection compositions, through which they function particularly effectively as carriers of the component (a).

Suitable relatively high molecular weight sulfonates generally exhibit a weight-average molecular weight (determined by means of gel permeation chromatography calibrated with polystyrenesulfonates) of at least ca. 1 kDa, preferably of at least ca. 2.5 kDa and in particular of at least ca. 5 kDa, for example a weight-average molecular weight of ca. 6-7 kDa (e.g. "Tamol NN" series), or of ca. 20 kDa (e.g. "Tamol NH" series). According to an additional aspect, suitable relatively high molecular weight sulfonates exhibit, for example, a number-average molecular weight (determined by means of gel permeation chromatography calibrated with polystyrenesulfonates) of ca. 1 kDa (e.g. "Tamol NN" series) or of ca. 2 kDa (e.g. "Tamol NH" series), so that the polydispersity index of suitable relatively high molecular weight sulfonates generally ranges from ca. 2 to 20 and preferably ranges from 5 to 15, for example is ca. 6 (e.g. "Tamol NN" series) or is ca. 20 (e.g. "Tamol NH" series). Additional properties of suitable relatively high molecular weight sulfonates are, for example, a bulk density of ca. 450-ca. 550 g/l for solids or a density of ca. 1.17-ca. 1.23 g/ml and a viscosity of ca. 20-ca. 80 mPa·s for liquids, and also a neutral to alkaline behavior (pH value in aqueous solution ca. 7-10).

According to a preferred embodiment of the invention, lignosulfonates are used.

Lignosulfonates are produced from lignin which, in turn, arises in plants, especially in woody plants, by polymerization from three types of phenylpropanol monomers:
A) 3-(4-hydroxyphenyl)-2-propen-1-ol (p-cumaryl alcohol),
B) 3-(3-methoxy-4-hydroxyphenyl)-2-propen-1-ol (coniferyl alcohol),
C) 3-(3,5-dimethoxy-4-hydroxyphenyl)-2-propen-1-ol (sinapyl alcohol).

The first step in the synthesis of the macromolecular lignin structure consists in enzymatically dehydrogenating these monomers, producing phenoxyl radicals. Random coupling reactions between these radicals lead to a three-dimensional amorphous polymer which, in contrast to most other biopolymers, exhibits no regularly arranged or repeated units. For this reason, no defined lignin structure can be mentioned, although various models for an "average" structure have been proposed. Since the monomers of the lignin comprise nine carbon atoms, the analytical data is often expressed in terms of $C_9$-formulae, e.g. $C_9H_{8.3}O_{2.7}(OCH_3)_{0.97}$ for lignin from *Picea abies* and $C_9H_{8.7}O_{2.9}(OCH_3)_{1.58}$ for lignin from *Eucalyptus regnans*.

The lack of uniformity of the lignin between plants of different taxa, just as between the different tissues, cells and cell wall layers of any one species, is familiar to a person skilled in the art. Lignins from coniferous trees, broad-leaved trees and grasses differ with regard to their content of guaiacyl (3-methoxy-4-hydroxyphenyl), syringyl (3,5-dimethoxy-4-hydroxyphenyl) and 4-hydroxyphenyl units. Lignins from coniferous trees are composed mainly of coniferyl alcohol, while lignins from broad-leaved trees are composed of guaiacyl and syringyl units in different ratios, the composition of the lignin being considerably more variable in broad-leaved trees than in coniferous trees. The methoxyl content of typical lignins from broad-leaved trees varies between 1.20 and 1.52 methoxyl groups per phenylpropane unit. Lignins from herbaceous plants generally have a low content of syringylpropanes with a ratio of methoxyl to $C_9$ units of less than 1.

The composition of the lignin also depends on the age, e.g. in poplars, the ratio of syringyl to guaiacyl in mature xylem is higher than in young xylem or phloem, and on the morphological position of the lignin in the cell wall. For example, in birch, the lignin in the secondary cell wall of fiber cells is composed mostly of syringyl units, while that in middle lamellae and cell corners of the fibers comprises mainly guaiacyl units. Lignin from wood under tension, in broad-leaved trees in the upper parts of the twigs and branches, comprises more syringylpropane units than the lignin from normal wood; wood under pressure, in coniferous trees in the lower parts of the twigs and branches, is, on the other hand, richer in 4-hydroxyphenyl units.

More than two-thirds of the phenylpropane units in lignin are linked via ether bonds and the remainder via carbon-carbon bonds.

The chemical behavior of the lignin is mainly determined by the presence of phenolic, benzylic and carbonylic hydroxyl groups, the frequency of which can vary depending on the abovementioned factors and the method of isolation.

Lignosulfonates are formed as byproducts in the manufacture of pulp under the action of sulfurous acid, which causes sulfonation and a certain amount of demethylation of the lignins. Like the lignins, they are varied in structure and composition. They are soluble in water over the entire pH range; on the other hand, they are insoluble in ethanol, acetone and other common organic solvents. The following $C_9$ formula is typical for coniferous lignosulfonates:

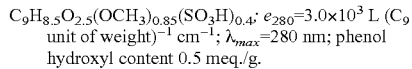

$C_9H_{8.5}O_{2.5}(OCH_3)_{0.85}(SO_3H)_{0.4}$; $e_{280}=3.0\times10^3$ L ($C_9$ unit of weight)$^{-1}$ cm$^{-1}$; $\lambda_{max}=280$ nm; phenol hydroxyl content 0.5 meq./g.

Lignosulfonates are only slightly surface-active. They have only a slight tendency to reduce the boundary tension between liquids and are not suitable for reducing the surface tension of water or for micelle formation. They can function as dispersants by adsorption/desorption and charge formation of substrates. However, their surface activity can be increased by introduction of long-chain alkyl amines into the lignin structure.

Methods for the isolation and purification of lignosulfonates are familiar to a person skilled in the art. In the Howard process, calcium lignosulfonates are precipitated by addition of an excess of lime to spent sulfite waste liquor. Lignosulfonates can also be isolated by formation of insoluble quaternary ammonium salts with long-chain amines. On the industrial scale, ultrafiltration and ion-exchange chromatography can be used for the purification of lignosulfonates.

Lignosulfonate series which can be used according to the invention are commercially available under a number of trade names, such as, e.g., Ameri-Bond, Dynasperse, Kelig, Lignosol, Marasperse, Norlig (Daishowa Chemicals), Lignosite (Georgia Pacific), Reax (Mead Westvaco), Wafolin, Wafex, Wargotan, Wanin, Wargonin (Holmens), Vanillex (Nippon Paper), Vanisperse, Vanicell, Ultrazine, Ufoxane (Borregaard), Serla-Bondex, Serla-Con, Serla-Pon, Serla-Sol (Serlachius), Collex, Zewa (Wadhof-Holmes) or Raylig (ITT Rayonier).

According to an additional preferred embodiment of the invention, synthetic polymeric sulfonates are used as component (b).

In this context, it is again particularly preferable for the relatively high molecular weight sulfonate to be a condensation product based on a sulfonated aromatic compound, an aldehyde and/or ketone and, if appropriate, on a compound chosen from nonsulfonated aromatic compounds, urea and urea derivatives.

In this context, it is particularly preferable for the sulfonated aromatic compound to be chosen from naphthalenesulfonic acids, indansulfonic acids, tetralinsulfonic acids, phenolsulfonic acids, di- and polyhydroxybenzenesulfonic acids, sulfonated ditolyl ethers, sulfomethylated 4,4'-dihydroxydiphenyl sulfones, sulfonated diphenylmethane, sulfonated biphenyl, sulfonated hydroxybiphenyl, sulfonated terpenyl and benzenesulfonic acids.

It is also particularly preferable for the aldehyde and/or the ketone to be chosen from aliphatic $C_1$-$C_5$-aldehydes or $C_3$-$C_5$-ketones. In this context, it is again particularly preferable for the aliphatic $C_1$-$C_5$-aldehyde to be formaldehyde.

Furthermore, it is particularly preferable for the nonsulfonated aromatic compound to be chosen from phenol, cresol and dihydroxydiphenylmethane. Furthermore, it is particularly preferable for the urea derivative to be chosen from dimethylolurea, melamine and guanidine.

In a particular embodiment, the condensation product comprises repetitive units according to formula (IIa):

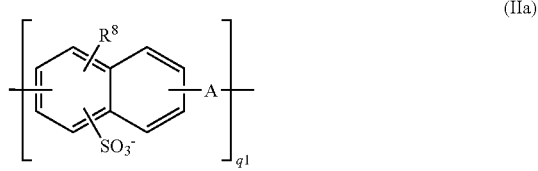

and/or formula (IIb):

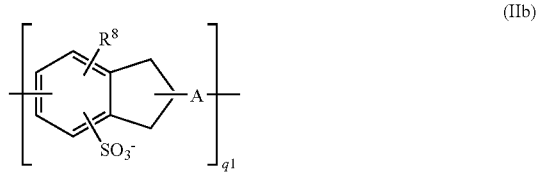

and/or formula (IIc):

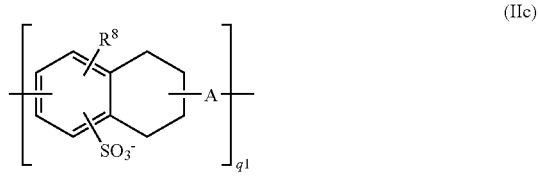

in which
$R^8$ is hydrogen, one or more hydroxyl groups or one or more $C_{1-8}$-alkyl radicals;
q1 corresponds to a value from 100 to $10^{10}$; and
A is methylene, 1,1-ethylene or a group of the formulae

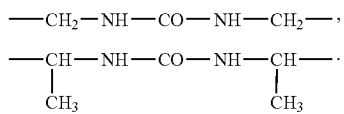

In the above formulae, the positions of the bonds are not specified.

Preferably, A is methylene. It is likewise preferable for $R^8$ to be hydrogen or up to 3 $C_{1-8}$-alkyl radicals, for example 1 or 2 $C_{1-4}$ alkyl radicals.

Such condensation products and the processes and devices for their preparation are familiar per se to a person skilled in the art.

In an additional particular embodiment, the condensation product comprises repetitive units according to formula (III):

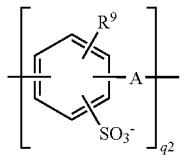

(III)

in which
$R^9$ is hydrogen, one or more hydroxyl groups or one or more $C_{1\text{-}8}$-alkyl radicals;
q2 corresponds to a value from 100 to $10^{10}$;
A is methylene, 1,1-ethylene or a group of the formulae

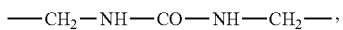

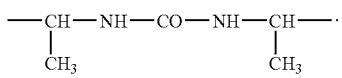

In the above formulae, the positions of the bonds are not specified.

It is preferable for $R^9$ to be a hydroxyl group.

In an additional particular embodiment, the sulfonate is chosen from the group consisting of condensation products of phenolsulfonic acid, formaldehyde and urea. Such condensation products preferably comprise repetitive units according to formula (IIIa):

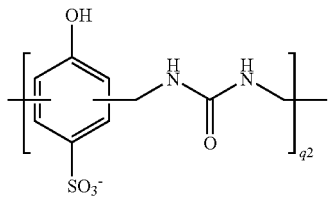

(IIIa)

in which
q2 corresponds to a value from 100 to $10^{10}$.

Such condensation products and the processes and devices for their preparation are also familiar per se to a person skilled in the art.

An additional embodiment of relatively high molecular weight sulfonates provides copolymers CP synthesized from ethylenically unsaturated monomers M, the monomers M constituting the copolymer CP comprising α) at least one monoethylenically unsaturated monomer M1 exhibiting at least one sulfonic acid group, and β) at least one neutral monoethylenically unsaturated monomer M2.

The copolymers CP are generally "random copolymers", i.e. the monomers M1 and M2 are randomly distributed along the polymer chain. In principle, alternating copolymers CP and block copolymers CP are also suitable.

The monomers M constituting the copolymer CP comprise according to the invention at least one monoethylenically unsaturated monomer M1 exhibiting at least one sulfonic acid group. The proportion of the monomers M1 to the monomers M in this context generally amounts to from 1 to 90% by weight, frequently from 1 to 80% by weight, in particular from 2 to 70% by weight and especially from 5 to 60% by weight, based on the total amount of monomers M.

In this context, all monoethylenically unsaturated monomers exhibiting at least one sulfonic acid group are suitable in principle as monomers M1. The monomers M1 can exist both in their acid form and in the salt form. The parts by weight given are based in this context on the acid form.

Examples of monomers M1 are styrenesulfonic acid, vinylsulfonic acid, allylsulfonic acid, methallylsulfonic acid and the monomers defined by the following general formula (V) and the salts of the abovementioned monomers.

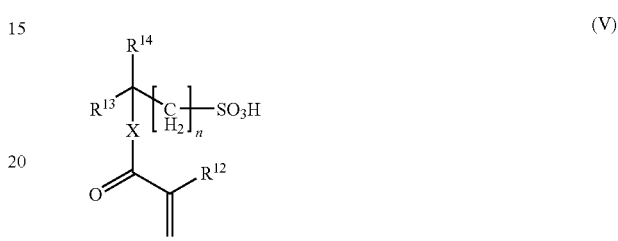

(V)

In formula (V):
n represents 0, 1, 2 or 3, in particular 1 or 2;
X represents O or $NR^{15}$;
$R^{12}$ represents hydrogen or methyl;
$R^{13}$ and $R^{14}$ represent, independently of one another, hydrogen or $C_1$-$C_4$-alkyl, in particular hydrogen or methyl, and
$R^{15}$ represents hydrogen or $C_1$-$C_4$-alkyl, in particular hydrogen.

Examples of monomers M1 of the general formula (V) are 2-acrylamido-2-methylpropanesulfonic acid, 2-methacrylamido-2-methylpropanesulfonic acid, 2-acrylamidoethanesulfonic acid, 2-methacrylamidoethanesulfonic acid, 2-acryloyloxyethanesulfonic acid, 2-methacryloyloxyethanesulfonic acid, 3-acryloyloxypropanesulfonic acid and 2-methacryloyloxypropanesulfonic acid.

In addition to the monomers M1, the monomers M constituting the copolymer CP comprise at least one neutral monoethylenically unsaturated monomer M2. "Neutral" means that the monomers M2 possess no functional group which reacts as an acid or base under aqueous conditions or is present in ionic form. The total amount of the monomers M2 generally comes to from 10 to 99% by weight, frequently from 20 to 99% by weight, in particular from 30 to 98% by weight and especially from 40 to 95% by weight, based on the total weight of the monomers M.

Examples of monomers M2 are those with limited solubility in water, e.g. a solubility in water of less than 50 g/l and in particular of less than 30 g/l (at 20° C. and 1013 mbar), and those with an elevated solubility in water, e.g. a solubility in water≧50 g/l, in particular ≧80 g/l (at 20° C. and 1013 mbar). Monomers with limited solubility in water are also described subsequently as monomers M2a. Monomers with elevated solubility in water are also described subsequently as monomers M2b.

Examples of monomers M2a are vinylaromatic monomers, such as styrene and styrene derivatives, such as α-methylstyrene, vinyltoluene, ortho-, meta- and para-methyl-styrene, ethylvinylbenzene, vinylnaphthalene, vinylxylene and the corresponding halogenated vinylaromatic monomers, α-olefins with from 2 to 12 carbon atoms, such as ethene, propene, 1-butene, 1-pentene, 1-hexene, isobutene, diisobutene and the like, dienes, such as butadiene and isoprene, vinyl esters of aliphatic $C_1$-$C_{18}$-carboxylic acids, such as vinyl acetate, vinyl propionate, vinyl laurate and vinyl stearate, vinyl halides, such as vinyl chloride, vinyl fluoride, vinylidene chloride or vinylidene fluoride, mono- and di-$C_1$-$C_{24}$-alkyl esters of monoethylenically unsaturated mono- and dicarboxylic acids, e.g. of acrylic acid, of methacrylic acid, of fumaric acid, of maleic acid or of itaconic acid, mono- and di-$C_5$-$C_{12}$-cycloalkyl esters of the abovementioned monoethylenically unsaturated mono- and dicarboxylic acids, mono- and diesters of the abovementioned monoethylenically unsaturated mono- and dicarboxylic acids with phenyl-$C_1$-$C_4$-alkanols or phenoxy-$C_1$-$C_4$-alkanols, and furthermore monoethylenically unsaturated ethers, in particular $C_1$-$C_{20}$-alkyl vinyl ethers, such as ethyl vinyl ether, methyl vinyl ether, n-butyl vinyl ether, octadecyl vinyl ether, triethylene glycol vinyl methyl ether, vinyl isobutyl ether, vinyl 2-ethylhexyl ether, vinyl propyl ether, vinyl isopropyl ether, vinyl dodecyl ether or vinyl tert-butyl ether.

The monomers M2a are preferably chosen from vinylaromatic monomers, esters of acrylic acid with $C_2$-$C_{10}$-alkanols, such as ethyl acrylate, n-butyl acrylate, 2-butyl acrylate, isobutyl acrylate, tert-butyl acrylate or 2-ethylhexyl acrylate, esters of acrylic acid with $C_4$-$C_{10}$-cycloalkanols, such as cyclohexyl acrylate, esters of acrylic acid with phenyl-$C_1$-$C_4$-alkanols, such as benzyl acrylate, 2-phenylethyl acrylate and 1-phenyl-ethyl acrylate, esters of acrylic acid with phenoxy-$C_1$-$C_4$-alkanols, such as 2-phenoxyethyl acrylate, esters of methacrylic acid with $C_1$-$C_{10}$-alkanols, in particular with $C_1$-$C_6$-alkanols, such as methyl methacrylate, ethyl methacrylate, n-butyl methacrylate, 2-butyl methacrylate, isobutyl methacrylate, tert-butyl methacrylate or 2-ethylhexyl methacrylate, esters of methacrylic acid with $C_4$-$C_{10}$-cycloalkanols, such as cyclohexyl methacrylate, esters of methacrylic acid with phenyl-$C_1$-$C_4$-alkanols, such as benzyl methacrylate, 2-phenylethyl methacrylate and 1-phenylethyl methacrylate, and esters of methacrylic acid with phenoxy-$C_1$-$C_4$-alkanols, such as 2-phenoxyethyl methacrylate. In a particularly preferred embodiment, the monomers M2a comprise up to at least 80%, based on the total amount of the monomers M2a, of and in particular exclusively esters of acrylic acid and/or of methacrylic acid with $C_1$-$C_6$-alkanols.

Neutral monoethylenically unsaturated monomers with increased solubility in water or even miscibility in water are known to a person skilled in the art, e.g. from Ullmann's Encyclopedia of Industrial Chemistry, "Polyacrylates", 5th ed. on CD-ROM, Wiley-VCH, Weinheim, 1997. Typical monomers M2b are hydroxy-$C_2$-$C_4$-alkyl esters of monoethylenically unsaturated monocarboxylic acids, in particular of acrylic acid and of methacrylic acid, such as 2-hydroxyethyl acrylate, 2-hydroxypropyl acrylate, 3-hydroxy-propyl acrylate, 2-hydroxybutyl acrylate, 4-hydroxybutyl acrylate, 2-hydroxyethyl methacrylate, 2-hydroxypropyl methacrylate, 3-hydroxypropyl methacrylate, 2-hydroxybutyl methacrylate or 4-hydroxybutyl methacrylate, furthermore amides of monoethylenically unsaturated monocarboxylic acids, such as acrylamide or methacrylamide, furthermore acrylonitrile and methacrylonitrile, N-vinyllactams, such as N-vinylpyrrolidone or N-vinylcaprolactam, N-vinylamides of aliphatic $C_1$-$C_4$-mono-carboxylic acids, such as N-vinylformamide or N-vinylacetamide, monoethylenically unsaturated monomers carrying urea groups, such as N-vinyl- and N-allylurea, and also derivatives of imidazolidin-2-one, e.g. N-vinyl- and N-allylimidazolidin-2-one, N-vinyloxyethylimidazolidin-2-one, N-allyloxyethylimidazolidin-2-one, N-(2-acrylamidoethyl)imidazolidin-2-one, N-(2-acryloyloxyethyl)imidazolidin-2-one, N-(2-methacrylamidoethyl)imidazolidin-2-one, N-(2-methacryloyloxyethyl)imidazolidin-2-one (=uredomethacrylate), N-[2-(acryloyloxyacetamido)ethyl]imidazolidin-2-one, N-[2-(2-acryloyloxyacetamido)ethyl]imidazolidin-2-one or N-[2-(2-methacryloyloxyacetamido)ethyl]imidazolidin-2-one; and the like. The monomers M2b are preferably chosen from hydroxy-$C_1$-$C_4$-alkyl esters of acrylic acid and of methacrylic acid, acrylamide, methacrylamide, acrylonitrile or N-vinyllactam, the hydroxy-$C_2$-$C_4$-alkyl esters of acrylic acid and of methacrylic acid being particularly preferred. In particular, the monomers M2b comprise up to at least 80% by weight, based on the total amount of the monomers M2b, of at least one hydroxy-$C_2$-$C_4$-alkyl ester of acrylic acid and/or of methacrylic acid.

Preferably, the monomers M2 comprise at least one of the abovementioned monomers M2a exhibiting, at 20° C. in water, a solubility of less than 50 g/l and in particular of less than 30 g/l. The proportion of the monomers M2a in the monomers M constituting the copolymer CP typically ranges from 10 to 99% by weight, frequently ranges from 20 to 99% by weight, in particular ranges from 30 to 98% by weight and especially ranges from 40 to 95% by weight, based on the total weight of the monomers M.

In a first preferred embodiment of the invention, the monomer M2a is sole or virtually sole monomer M2 and amounts to at least 95% by weight and in particular at least 99% by weight of the monomers M2.

In a second preferred embodiment of the invention, the monomers M2 comprise, in addition to the monomer M2a, at least one monomer M2b exhibiting, at 20° C. in water, a solubility of at least 50 g/l and in particular of at least 80 g/l. Correspondingly, the monomers M constituting the copolymer CP comprise, in addition to the monomer M1, both at least one of the abovementioned monomers M2a, in particular at least one of the monomers M2a mentioned as preferred, and at least one of the abovementioned monomers M2b, in particular at least one of the monomers M2b mentioned as preferred.

The total amount of the monomers M1+M2b will frequently not exceed 90% by weight, in particular 80% by weight and especially 70% by weight, based on the total amount of the monomers M, and ranges in particular from 10 to 90% by weight, in particular from 20 to 80% by weight and especially from 30 to 70% by weight, based on the total amount of the monomers M. Correspondingly, the monomers M2a frequently come to at least 10% by weight, in particular at least 20% by weight and especially at least 30% by weight, e.g. from 10 to 90% by weight, in particular from 20 to 80% by weight and especially from 30 to 70% by weight, based on the total amount of the monomers M.

In this second particularly preferred embodiment, the monomers M1 preferably come to from 1 to 80% by weight, in particular from 2 to 70% by weight and particularly preferably from 5 to 60% by weight, the monomers M2a preferably come to from 10 to 90% by weight, in particular from 20 to 80% by weight and particularly preferably from 30 to 70% by weight, and the monomers M2b preferably come to from 5 to 89% by weight, in particular from 10 to 78% by weight and particularly preferably from 20 to 65% by weight, based on the total amount of the monomers M. Particular preference is given among these to copolymers CP, the constituent monomers M of which comprise, as monomers M1, at least one monomer of the formula (V), as monomers M2a, at least one monomer chosen from esters of acrylic acid with $C_2$-$C_{10}$-alkanols and esters of methacrylic acid with $C_1$-$C_{10}$-alkanols and, as monomers M2b, at least one monomer chosen from hydroxy-$C_2$-$C_4$-alkyl esters of acrylic acid and of methacrylic acid.

In addition, the monomers M constituting the copolymer can comprise yet further monomers M3 differing from the monomers M1 and M2. The proportion of the monomers M3 in the total amount of the monomers M preferably comes to not more than 40% by weight, in particular not more than 20% by weight. In a preferred embodiment, the monomers comprise no or not more than 3% by weight, especially not more than 1% by weight, of monomers M3 differing from the monomers M1 and M2.

The monomers M3 include monoethylenically unsaturated monomers with at least one carboxylic group, in particular monoethylenically unsaturated mono- and dicarboxylic acids with from 3 to 6 carbon atoms (monomers M3a), such as acrylic acid, methacrylic acid, vinylacetic acid, crotonic acid, fumaric acid, maleic acid, itaconic acid and the like, and the anhydrides of the abovementioned monoethylenically unsaturated dicarboxylic acids, the proportion of the monomers M3a generally not exceeding 20% by weight and in particular 10% by weight, based on the total amount of monomers M.

The monomers M3 furthermore include polyethylenically unsaturated monomers (M3b). The proportion of such monomers M3 will generally be not more than 2% by weight and in particular not more than 0.5% by weight, based on the total amount of monomers M. Examples of these are vinyl and allyl esters of monoethylenically unsaturated carboxylic acids, such as allyl acrylate and allyl methacrylate, di- and polyacrylates of di- or polyols, such as ethylene glycol diacrylate, ethylene glycol dimethacrylate, butanediol diacrylate, butanediol dimethacrylate, hexanediol diacrylate, hexanediol dimethacrylate, triethylene glycol diacrylate, triethylene glycol dimethacrylate, tris(hydroxymethyl)ethane triacrylate and trimethacrylate, or pentaerythritol triacrylate and trimethacrylate, and furthermore the allyl and methallyl esters of polyfunctional carboxylic acids, such as diallyl maleate, diallyl fumarate or diallyl phthalate. Typical monomers M3b are also compounds such as divinylbenzene, divinylurea, diallylurea, triallyl cyanurate, N,N'-divinyl- and N,N'-diallylimidazolidin-2-one, and also methylenebisacrylamide and methylenebismethacrylamide.

Preference is furthermore given according to the invention to copolymers CP exhibiting a number-average molecular weight $M_n$ ranging from 1000 to 500 000 daltons, in particular from 2000 to 50 000 daltons and especially from 5000 to 20 000 daltons. The weight-average molecular weight frequently ranges from 2000 to 1 000 000 daltons, in particular from 4000 to 100 000 daltons and especially from 10 000 to 50 000 daltons. The ratio $M_w/M_n$ frequently ranges from 1.1:1 to 10:1, in particular from 1.2:1 to 5:1.

The molar masses $M_w$ and $M_n$ and the lack of uniformity of the polymers are determined by size exclusion chromatography (=gel permeation chromatography or just GPC). Commercial poly(methyl methacrylate) (PMMA) standard units can be used as calibration material.

Generally, the copolymer according to the invention will exhibit a glass transition temperature $T_g$ ranging from $-80°$ C. to $160°$ C. and frequently ranging from $-40°$ C. to $+100°$ C. The term "glass transition temperature $T_g$" is understood here to mean the "midpoint temperature" determined according to ASTM D 3418-82 by differential scanning calorimetry (DSC) (cf. Ullmann's Encyclopedia of Industrial Chemistry, 5th Edition, Volume A 21, VCH Weinheim, 1992, p. 169, and also Zosel, Farbe und Lack, 82 (1976), pp. 125-134, see also DIN 53765).

In this context, it proves to be helpful to estimate the glass transition temperature $T_g$ of the copolymer CP with the help of the Fox equation (T. G. Fox, Bull. Am. Phys. Soc. (Ser. II), 1, 123 [1956], and Ullmann's Encyclopedia of Industrial Chemistry, Weinheim (1980), pp. 17-18) from the glass transition temperatures of the respective homopolymers of the monomers M constituting the polymer. The latter are known, e.g., from Ullmann's Encyclopedia of Industrial Chemistry, VCH, Weinheim, Vol. A 21 (1992), p. 169, or from J. Brandrup and E. H. Immergut, Polymer Handbook, 3rd ed., J. Wiley, New York, 1989.

The copolymers CP according to the invention are in some cases known from PCT/EP04/011797 or can be prepared according to conventional methods by radical polymerization of the monomers M. The polymerization can be carried out by free radical polymerization or by controlled radical polymerization processes. The polymerization using one or more initiators and can be carried out as solution polymerization, as emulsion polymerization, as suspension polymerization, as precipitation polymerization or as bulk polymerization. The polymerization can be carried out batchwise, semicontinuously or continuously.

The reaction times generally range between 1 and 12 hours. The temperature range in which the reactions can be carried out generally extends from 20 to 200° C., preferably from 40 to 120° C. The polymerization pressure is of secondary importance and can be carried out in the range from standard pressure or slight negative pressure, e.g. >800 mbar, or under positive pressure, e.g. up to 10 bar, it being possible for higher or lower pressures likewise to be used.

Conventional radical-forming substances are used as initiators for the radical polymerization. Preference is given to initiators from the group of the azo compounds, of the peroxide compounds or of the hydroperoxide compounds. Mention may be made, by way of examples, of acetyl peroxide, benzoyl peroxide, lauryl peroxide, tert-butylperoxy isobutyrate, caproyl peroxide, cumene hydroperoxide, 2,2'-azobisisobutyronitrile, 2,2'-azobis(2-methylbutyronitrile), 2,2'-azobis[2-methyl-N-(2-hydroxyethyl)propionamide], 1,1'-azobis(1-cyclohexanecarbonitrile), 2,2'-azobis(2,4-dimethylvaleronitrile) or 2,2'-azobis(N,N'-dimethyleneisobutyroamidine). Azobisisobutyronitrile (AIBN) is particularly preferred. The initiator is normally used in an amount of from 0.02 to 5% by weight and in particular from 0.05 to 3% by weight, based on the amount of the monomers M. The optimum amount of initiator naturally depends on the initiator system used and can be determined by a person skilled in the art in routine experiments. The initiator can be partially or completely provided within the reaction vessel. Preferably, the bulk of the initiator, in particular at least 80%, e.g. from 80 to 100%, of the initiator, is added to the polymerization reactor in the course of the polymerization.

The molecular weight of the copolymer CP can self-evidently be adjusted by addition of a small amount of regulators, e.g. from 0.01 to 5% by weight, based on the polymerizing monomers M. Suitable regulators are in particular organic thio compounds, e.g. mercaptoalcohols, such as mercaptoethanol, mercaptocarboxylic acids, such as thioglycolic acid or mercaptopropionic acid, or alkyl mercaptans, such as dodecyl mercaptan, and furthermore allyl alcohols and aldehydes.

The copolymers CP are prepared in particular by radical solution polymerization in a solvent. Examples of solvents are water, alcohols, such as, e.g., methanol, ethanol, n-propanol and isopropanol, dipolar aprotic solvents, e.g. N-alkyllactams, such as N-methylpyrrolidone (NMP) or N-ethylpyrrolidone, furthermore dimethyl sulfoxide (DMSO) or N,N-dialkylamides of aliphatic carboxylic acids, such as N,N-dimethyl-formamide (DMF) or N,N-dimethylacetamide, or furthermore aromatic, aliphatic and cycloaliphatic hydrocarbons which may be halogenated, such as hexane, chlorobenzene, toluene or benzene. Preferred solvents are isopropanol, methanol, toluene, DMF, NMP, DMSO and hexane. DMF is particularly preferred.

As salts, the sulfonates comprise cations in a stoichiometric amount. Examples of suitable cations are alkali metal cations, such as $Na^+$ or $K^+$, alkaline earth metal ions, such as $Ca^{2+}$ and $Mg^{2+}$, furthermore ammonium ions, such as $NH_4^+$, tetraalkylammonium cations, such as tetramethylammonium, tetraethylammonium and tetrabutylammonium, or furthermore protonated primary, secondary and tertiary amines, in particular those carrying 1, 2 or 3 radicals chosen from $C_1$-$C_{20}$-alkyl groups and hydroxyethyl groups, e.g. the protonated forms of mono-, di- and tributylamine, propylamine, diisopropylamine, hexylamine, dodecylamine, oleylamine, stearylamine, ethoxylated oleylamine, ethoxylated stearylamine, ethanolamine, diethanolamine, triethanolamine or N,N-dimethylethanolamine.

In a preferred embodiment of the invention, the sulfonate is an ammonium, alkali metal, alkaline earth metal or transition metal sulfonate.

In this context, it is particularly preferable each time for the alkali metal to be sodium or potassium, for the alkaline earth metal to be calcium or magnesium and for the transition metal to be copper.

Mixtures of different sulfonates can also be used as component (b).

Suitable sulfonates are familiar to a person skilled in the art and are available, e.g. under the names "Tamol" and "Setamol", from BASF.

Examples of polymers comprising sulfonic acid which are suitable in principle as component (b) are also mentioned in EP 707 445.

In this context, it is particularly preferable for the plant protection composition to comprise at least 15% by weight, preferably at least 25% by weight and in particular at least 30% by weight of relatively high molecular weight sulfonate.

In this context, it is also particularly preferable for the plant protection composition to comprise at most 80% by weight, preferably at most 70% by weight and in particular at most 55% by weight of relatively high molecular weight sulfonate.

The plant protection compositions according to the invention comprise relatively high amounts of polyalkoxylate. It is preferable, based on the amount of relatively high molecular weight sulfonate, for the ratio by weight of liquid or low melting point polyalkoxylate to relatively high molecular weight sulfonate to be at least 3:10, preferably at least 1:3 and particularly preferably 1:2. The ratio of liquid or low melting point polyalkoxylate to relatively high molecular weight sulfonate should, though, not be more than 3:1, preferably not be more than 2:1.

In one embodiment of the invention, a portion of the sulfonate in the carrier component (b) can be replaced by inorganic solid. In this embodiment, the component (b), in addition to the relatively high molecular weight sulfonate (b1), also comprises inorganic solid (b2).

Possible inorganic solids in the carrier component (b) are in particular those which are conventionally used in solid plant protection compositions for taking up liquid or low melting point, in particular oily, auxiliaries, such as the polyalkoxylates according to the invention (carriers). In this context, inorganic solids which make possible adsorption of aforementioned auxiliaries (sorbent materials) are mainly concerned.

Suitable inorganic solids are generally sparingly soluble or insoluble in water, i.e. at least 100, generally at least 1000 and in particular at least 10 000 parts of water are necessary to dissolve one part of inorganic solid at 20° C. However, the sparingly soluble or even water-insoluble inorganic solids can be swellable in water.

The inorganic solids include in particular substances based on aluminum oxide, in particular aluminum oxide and bauxite, and substances based on silicon dioxide, in particular silicates and silicate minerals, above all diatomaceous earths (kieselguhr, diatomite), silicas, pyrophyllite, talc, mica and clays, such as kaolinite, bentonite, montmorillonite and attapulgite. Some inorganic salts, for example alkaline earth metal carbonates, in particular calcium carbonates (limestone, chalk) and magnesium carbonates, and also calcium magnesium carbonates, and alkaline earth metal sulfates, in particular calcium sulfates (e.g. gypsum), are also suitable in principle. Mention may be made, among the silicates, for example, of the products of the Sipernat series (Degussa), in particular Sipernat 22S or 50S, which can typically be used for these purposes.

The proportion of the inorganic solids suitable as component (b2) listed above can according to the invention, though, be chosen to be comparatively low since the relatively high molecular weight sulfonates function essentially as carriers of the polyalkoxylates. In addition, further advantages become apparent on avoiding high proportions of inorganic solids.

To this effect, the weight-related proportion of the relatively high molecular weight sulfonate in the component (b) is generally greater than the weight-related proportion of inorganic solid; according to the invention, the weight ratio of relatively high molecular weight sulfonate to inorganic solid is preferably at least 2, preferably at least 5 and in particular at least 10.

In particular, it is preferable for the composition altogether to comprise less than 10% by weight, in particular less than 5% by weight, of aluminium oxide based substances and particularly preferable for the composition altogether to be essentially free of aluminum oxide based substances.

It is also preferable for the composition altogether to comprise less than 5% by weight, in particular less than 2% by weight, of diatomaceous earths and particularly preferable for the composition altogether to be essentially free of diatomaceous earths. It is also preferable for the composition altogether to comprise less than 5% by weight, in particular less than 1% by weight, of kaolinite and particularly preferable for the composition altogether to be essentially free of kaolinite. It is also preferable for the composition altogether to comprise less than 5% by weight, in particular less than 1% by weight, of bentonites and particularly preferable for the composition altogether to be essentially free of bentonites.

It is also preferable for the composition altogether to comprise less than 7.5% by weight, in particular less than 1.5% by weight, of clays and particularly preferable for the composition to be essentially free of clays.

It is also preferable for the composition altogether to comprise less than 15% by weight, in particular less than 2% by weight, of substances based on silicon dioxide and particularly preferable for the composition to be essentially free of substances based on silicon dioxide.

According to a particular embodiment, the composition comprises altogether less than 15% by weight, in particular less than 10% by weight and particularly preferably less than 5% by weight of the following inorganic solids: substances based on aluminum oxide, in particular aluminum oxide and bauxite, and substances based on silicon dioxide, in particular silicates and silicate minerals, above all diatomaceous earths (kieselguhr, diatomite), silicas, pyrophillite, talc, mica and clays, such as kaolinite, bentonite, montmorillonite and attapulgite.

It is preferable for the composition altogether to comprise less than 1% by weight of sorbent materials and particularly preferable for the composition altogether to be essentially free of sorbent materials.

Furthermore, it is preferable for the composition altogether to comprise less than 5% by weight, in particular less than 1% by weight, of calcium carbonate and particularly preferable for the composition altogether to be essentially free of calcium carbonate. Furthermore, it is also preferable for the composition altogether to comprise less than 5% by weight, in particular less than 1% by weight, of magnesium carbonate and particularly preferable for the composition altogether to be essentially free of magnesium carbonate.

According to a particular embodiment, the composition comprises altogether less than 10% by weight, in particular less than 5% by weight and particularly preferably less than 1% by weight of the following inorganic solids: alkali metal and alkaline earth metal carbonates, in particular calcium carbonates (limestone, chalk) and magnesium carbonates, as well as calcium magnesium carbonates, and alkali metal and alkaline earth metal sulfates, in particular calcium sulfates (e.g. gypsum).

In this context, it is very particularly preferable for the composition to comprise altogether at most 15% by weight, preferably altogether at most 10% by weight and especially at most 5% by weight, e.g. at most 1% by weight, of inorganic solid and especially for the carrier component (b) to be essentially free of inorganic solid.

According to a particular embodiment, the present invention relates to a plant protection composition which, in addition to the components a) and b), can comprise additional auxiliary as component c).

The optional component (c) can serve a multitude of purposes. Generally, component (c) accordingly is composed of a combination of several materials with different functions and properties. The choice of suitable auxiliaries is made conventionally by a person skilled in the art according to the requirements.

The following are suitable in particular as component (c):
c1) surface-active auxiliaries;
c2) suspension agents, antifoaming agents, retention agents, pH buffers, drift retardants and other auxiliaries for improving the handleability and/or physical properties of the composition; and
c3) chelating agents.

The term "surface-active auxiliaries" (c1) describes here surface-active agents such as surfactants, dispersants, emulsifiers or wetters.

Anionic, cationic, amphoteric and nonionic surfactants can be used in principle.

The anionic surfactants include, for example:
carboxylates, in particular alkali metal, alkaline earth metal and ammonium salts of fatty acids;
acyl glutamates;
sarcosinates, e.g. sodium lauryl sarcosinate;
taurates;
methylcelluloses;
alkyl phosphates, e.g. monophosphoric acid alkyl esters and hypophosphoric acid alkyl esters;
sulfates;
monomeric sulfonates, in particular alkyl- and alkylarylsulfonates, above all alkali metal, alkaline earth metal and ammonium salts of arylsulfonic acids and alkyl-substituted arylsulfonic acids, alkylbenzenesulfonic acids, such as, for example, phenolsulfonic acids, naphthalene- and dibutylnaphthalenesulfonic acids, or dodecylbenzenesulfonates, alkylnaphthalenesulfonates, alkyl methyl ester sulfonates, or mono- or dialkylsuccinic acid ester sulfonates;
protein hydrolysates and spent lignosulfite waste liquors.

The cationic surfactants include, for example:
quaternary ammonium salts, in particular alkyltrimethylammonium and dialkyl-dimethylammonium halides and alkyl sulfates, and
pyridine and imidazoline derivatives, in particular alkylpyridinium halides.

The nonionic surfactants include in particular:
glycerol esters, such as, for example, glycerol monostearate;
sugar surfactants, in particular sorbitol esters, such as, for example, sorbitan fatty acid esters (sorbitan monooleate, sorbitan tristearate), and esters of mono- or polyhydric alcohols, such as alkyl(poly)glycosides and N-alkylgluconamides;
alkyl methyl sulfoxides;
alkyldimethylphosphine oxides, such as, for example, tetradecyldimethyl-phosphine oxide;
di-, tri- and multiblock polymers of the $(AB)_x$, ABA and BAB type, e.g. poly-styrene-block-polyethylene oxide, and AB comb polymers, e.g. polymethacrylate-comb-polyethylene oxide, and in particular ethylene oxide/propylene oxide block copolymers or their end-capped derivatives.

The amphoteric surfactants include, for example:
sulfobetaines;
carboxybetaines, and
alkyldimethylamine oxides, e.g. tetradecyldimethylamine oxide.

Additional surfactants which may be mentioned here by way of example, without being able to be unambiguously assigned to one of the groups mentioned, comprise:
perfluorinated surfactants,
silicone surfactants,
phospholipids, such as, e.g., lecithin or chemically modified lecithins,
amino acid surfactants, e.g. N-lauroylglutamate, and
surface-active homo- and copolymers, e.g. polyvinylpyrrolidone, polyacrylic acids in the form of their salts, polyvinyl alcohol, polypropylene oxide, poly-ethylene oxide, maleic anhydride/isobutene copolymers and vinylpyrrolidone/vinyl acetate copolymers.

Furthermore, the following are possible, inter alia, as wetters: dioctyl sulfosuccinate (e.g., "Pelex OTP"), dialkylsulfonimide ("Leophen RBD"), diisobutylnaphthalene-sulfonate ("Nekal BX"), various alkylalkynols ("Surfynol", Bisterfeld), alkylarylphenol ether phosphate esters ("Phospholan PNP") and polyethylene glycol ("Pluriol"), and also combinations of the materials mentioned.

The proportion of the surface-active auxiliary component (c1) in the total weight of the composition, if present, is generally up to 25% by weight, preferably up to 20% by weight, in particular up to 15% by weight and especially up to 10% by weight, based on the total weight of the composition.

Such surface-active auxiliary components are in some cases contained in active agent suspensions and preconcentrates which are used in combination with the ingredients according to the invention. Alternatively, they can be added separately in a suitable stage of the preparation of the composition.

The antifoaming agents include in particular those of the silicone type, for example the Silicon SL sold by Wacker and the like.

The suspension agents, retention agents, pH buffers and drift retardants comprise a multitude of possible substances. They are familiar to a person skilled in the art.

Additional auxiliaries from (c2) are, e.g., antidusting agents, supporting substances, polymers for improving the structure of granules, coating agents or polymeric flow improvers for granules. Such auxiliaries are described in the state of the art and are familiar to a person skilled in the art. Hydrophilic pyrogenic silicas, such as the Aerosil brands (Degussa), can also function as auxiliaries and/or antiblocking agents.

The proportion of the surface-active auxiliary component (c2) in the total weight of the composition, if present, is generally up to 15% by weight, preferably up to 10% by weight and in particular up to 5% by weight, based on the total weight of the composition.

Preferred chelating agents are compounds which complex heavy metals and in particular transition metals, e.g. EDTA and its derivatives.

If present, the proportion of the component (c3) in the total weight of the composition is generally from 0.001 to 0.5% by weight, preferably from 0.005 to 0.2% by weight and in particular from 0.01 to 0.1% by weight.

It is generally preferable for the composition altogether to comprise at most 60% by weight, preferably at most 45% by weight and in particular at most 30% by weight of additional auxiliary (c).

Typically, the ratio by weight of (a) and (b) to (c) is at least 3, preferably at least 5.

According to a particular embodiment, the present invention relates to a solid plant protection composition which, in addition to the components a), b) and, if appropriate, c), can comprise water-soluble inorganic salt as component d).

An inorganic salt is then water-soluble if less than 20 parts of water, in particular less than 10 parts of water, are necessary to dissolve one part of inorganic salt at 20° C. Possible water-soluble inorganic salts of the component (d) are in particular those which can be used agriculturally, for example minerals which can be made use of by plants and trace elements.

Suitable water-soluble inorganic salts occur in particular among alkali metal and ammonium salts, particularly preferably sodium, potassium and ammonium sulfates, chlorides, carbonates, nitrates and phosphates, particularly preferably again ammonium sulfate and ammonium hydrogensulfate, and their mixtures. According to a particular embodiment, the component (d) is composed essentially of ammonium sulfate.

If present, the proportion of the component (d) in the total weight of the composition can be up to 65% by weight. Preferably, its proportion in the total weight of the composition is up to 50% by weight, preferably up to 28.5% by weight and particularly preferably up to 25% by weight, e.g. 0% by weight-17.5% by weight.

The component (d) is particularly suitable as base solid for fluidized bed granules. The water-soluble inorganic salt can accordingly serve as nucleus for the forming process during the fluidized bed drying since, in the fluidized bed drying, no de novo formation of defined particles from the fluid phase is possible without introduction of a solid core for attachment to or a fluidized bed process without addition of solid nuclei does not result in usable particle size distributions.

Solid plant protection compositions with relatively low proportions of component (d) certainly represent a preferred embodiment. To this effect, the proportion of the component (d) in the overall composition is from 0 to 10% by weight, preferably from 0 to 5% by weight and in particular from 0 to 2% by weight, e.g. 0% by weight-1% by weight. In this embodiment, the water-soluble inorganic salts nevertheless present are not generally of particular importance in the sense of the formulation. Typically, they are frequently included as a result of the preparation, i.e. they are incorporated together with other components according to the invention.

Consequently, it is preferable for the composition altogether to comprise less than 5% by weight, in particular less than 2% by weight, of sodium chloride and particularly preferable for the composition altogether to be essentially free of sodium chloride. It is consequently also preferable for the composition altogether to comprise less than 5% by weight, in particular less than 2% by weight, of potassium chloride and particularly preferable for the composition altogether to be essentially free of potassium chloride. It is consequently also preferable for the composition altogether to comprise less than 5% by weight, in particular less than 2% by weight, of sodium carbonate and particularly preferable for the composition altogether to be essentially free of sodium carbonate. It is consequently also preferable for the composition altogether to comprise less than 5% by weight, in particular less than 2% by weight, of potassium hydrogenphosphate and particularly preferable for the composition altogether to be essentially free of potassium hydrogenphosphate.

According to a particular embodiment, the composition altogether comprises less than 10% by weight, in particular less than 5% by weight and particularly preferably less than 1% by weight of the following water-soluble inorganic solids: alkali metal and alkaline earth metal halides, in particular sodium chloride and potassium chloride, alkali metal sulfates, e.g. sodium sulfate, alkali metal carbonates, e.g. sodium carbonate, and alkali metal and alkaline earth metal phosphates, in particular potassium hydrogenphosphate.

In this context, any substance may be described as plant protection active agent (pesticide) of the component (e) which has the purpose or effect of preventing infection of a plant by any pest or of repelling, deterring or destroying the pest or of reducing in another way the damage caused by it. As stated above, plant pests can belong to different groups of organisms; the higher animals, in particular insects and acarids, include numerous important pests, as do nematodes and snails; vertebrates, such as mammals and birds, are today of secondary importance in industrialized countries. Numerous groups of microbes, including fungi, bacteria, inclusive of mycoplasmas, viruses and viroids, comprise pests, and even weeds, which compete with useful plants for limited habitat and other resources, can be classed as pests in the broad sense. Pesticides comprise in particular avicides, acaricides, desiccants, bactericides, chemosterilants, defoliants, antifeedants, fungicides, herbicides, herbicide safeners, insect attractants, insecticides, insect repellents, molluscicides, nematicides, mating disrupters, plant activators, plant growth regulators, rodenticides, mammal repellents, synergists, bird repellents and virucides.

Pesticides comprise, classified according to chemical classes, in particular acylalanine fungicides, acylamino acid fungicides, aliphatic amide organothiophosphate insecticides, aliphatic organothiophosphate insecticides, aliphatic nitrogen fungicides, amide fungicides, amide herbicides, anilide fungicides, anilide herbicides, inorganic fungicides, inorganic herbicides, inorganic rodenticides, antiauxins, antibiotic acaricides, antibiotic fungicides, antibiotic herbicides, antibiotic insecticides, antibiotic nematicides, aromatic acid fungicides, aromatic acid herbicides, arsenical herbicides, arsenical insecticides, arylalanine herbicides, aryloxyphenoxypropionic acid herbicides, auxins, avermectin acaricides, avermectin insecticides, benzamide fungicides, benzanilide fungicides, benzimidazole fungicides, benzimidazole precursor fungicides, benzimidazolylcarbamate fungicides, benzoic acid herbicides, benzofuranyl alkylsulfonate herbicides, benzofuranyl methylcarbamate insecticides, benzothiazole fungicides, benzothiopyran organothiophosphate insectides, benzotriazine organothio-phosphate insecticides, benzoylcyclohexanedione herbicides, bipyridylium herbicides, bridged diphenyl acaricides, bridged diphenyl fungicides, carbamate acaricides, carbamate fungicides, carbamate herbicides, carbamate insecticides, carbamate nematicides, carbanilate fungicides, carbanilate herbicides, quinolinecarboxylate herbicides, quinoline fungicides, quinone fungicides, quinoxaline acaricides, quinoxaline organothiophosphate insecticides, quinoxaline fungicides, chitin synthesis inhibitors, chloracetanilide herbicides, chloronicotinyl insecticides, chloropyridine herbicides, chlorotriazine herbicides, conazole fungicides, coumarin rodenticides, cyclodithiocarbamate fungicides, cyclohexane oxime herbicides, cyclopropylisoxazole herbicides, cytokinins, diacylhydrazine insecticides, dicarboximide fungicides, dicarboximide herbicides, dichlorophenyl dicarboximide fungicides, dimethylcarbamate insecticides, dinitroaniline herbicides, dinitrophenol acaricides, dinitrophenol fungicides, dinitrophenol herbicides, dinitrophenol insecticides, diphenyl ether herbicides, dithiocarbamate fungicides, dithiocarbamate herbicides, defoliants, ethylene releasers, fluorine insecticides, furamide fungicides, furanilide fungicides, gibberellins, halogenated aliphatic herbicides, urea fungicides, urea herbicides, urea insecticides, urea rodenticides, moulting hormones, moulting hormone mimics, moulting inhibitors, heterocyclic organothiophosphate insecticides, imidazole fungicides, imidazolinone herbicides, indandione rodenticides, insect growth regulators, isoindole organothiophosphate insecticides, isoxazole organothiophosphate insecticides, juvenile hormones, juvenile hormone mimics, copper fungicides, macrocyclic lactone acaricides, macrocyclic lactone insecticides, methoxytriazine herbicides, methylthiotriazine herbicides, milbemycin acaricides, milbemycin insecticides, mite growth regulators, morphactins, morpholine fungicides, nereistoxin analogues, nicotinoid insecticides, nitrile herbicides, nitroguanidine insecticides, nitromethylene insecticides, nitrophenyl ether herbicides, organochlorine acaricides, organochlorine insecticides, organochlorine rodenticides, organophosphate acaricides, organophosphate insecticides, organophosphate nematicides, organophosphorus acaricides, organophosphorus fungicides, organophosphorus herbicides, organophosphorus insecticides, organophosphorus nematicides, organophosphorus rodenticides, organothiophosphate acaricides, organothiophosphate insecticides, organothiophosphate nematicides, organotin acaricides, organotin fungicides, oxadiazine insecticides, oxathiine fungicides, oxazole fungicides, oxime carbamate acaricides, oxime carbamate nematicides, oxime carbamate insecticides, oxime organothiophosphate insecticides, botanical insecticides, botanical rodenticides, phenoxybutyric acid herbicides, phenoxyacetic acid herbicides, phenoxy herbicides, phenoxypropionic acid herbicides, phenylenediamine herbicides, phenyl ethylphosphonothioate insecticides, phenylurea herbicides, phenyl methylcarbamate insecticides, phenyl organothiophosphate insecticides, phenyl phenylphosphonothioate insecticides, phenyl pyrazolyl ketone herbicides, phenylsulfamide acaricides, phenylsulfamide fungicides, phosphonate acaricides, phosphonate insecticides, phosphonothioate insecticides, phosphoramidate insecticides, phosphoramidothioate acaricides, phosphoramidothioate insecticides, phosphorodiamide acaricides, phosphorodiamide insecticides, phthalate herbicides, phthalimide acaricides, phthalimide fungicides, phthalimide insecticides, picolate herbicides, polymeric dithiocarbamate fungicides, polysulfide fungicides, precocenes, pyrazole acaricides, pyrazole fungicides, pyrazole insecticides, pyrazolopyrimidine organothiophosphate insecticides, pyrazolyloxyacetophenone herbicides, pyrazolylphenyl herbicides, pyrethroid acaricides, pyrethroid ester acaricides, pyrethroid ester insecticides, pyrethroid ether acaricides, pyrethroid ether insecticides, pyrethroid insecticides, pyridazine herbicides, pyridazinone herbicides, pyridine fungicides, pyridine herbicides, pyridine organothiophosphate insecticides, pyridylmethylamine insecticides, pyrimidinamine acaracides, pyrimidinamine insecticides, pyrimidinamine rodenticides, pyrimidinediamine herbicides, pyrimidine organothiophosphate insecticides, pyrimidine fungicides, pyrimidinyloxybenzoic acid herbicides, pyrimidinylsulfonylurea herbicides, pyrimidinylthiobenzoic acid herbicides, pyrrole acaricides, pyrrole fungicides, pyrrole insecticides, quaternary ammonium herbicides, strobilurin fungicides, sulfite ester acaricides, sulfonamide fungicides, sulfonamide herbicides, sulfonanilide fungicides, sulfonanilide herbicides, sulfonylurea herbicides, tetrazine acaracides, tetronate acaricides, tetronate insecticides, thiadiazole organothiophosphate insecticides, thiadiazolylurea herbicides, thiazole fungicides, thiocarbamate acaricides, thiocarbamate fungicides, thiocarbamate herbicides, thiocarbonate herbicides, thiourea acaricides, thiourea herbicides, thiourea rodenticides, thiophene fungicides, triazine fungicides, triazine herbicides, triazinone herbicides, triazinylsulfonylurea herbicides, triazole fungicides, triazole herbicides, triazolone herbicides, triazolopyrimidine herbicides, triazole organothiophosphate insecticides, uracil herbicides, valinamide fungicides, growth inhibitors, growth stimulators, growth retardants and xylylalanine fungicides.

The pesticide for use according to the invention is chosen in particular from fungicides (e1), herbicides (e2) and insecticides (e3).

Fungicides comprise, for example, aliphatic nitrogen fungicides, such as butylamine, cymoxanil, dodicin, dodine, guazatine or iminoctadine; amide fungicides, such as carpropamid, chloraniformethan, cyflufenamid, diclocymet, ethaboxam, fenoxanil, flumetover, furametpyr, mandipropamid, penthiopyrad, prochloraz, quinazamid, silthiofam or triforine; in particular acylamino acid fungicides, such as benalaxyl, benalaxyl-M, furalaxyl, metalaxyl, metalaxyl-M or pefurazoate; anilide fungicides, such as benalaxyl, benalaxyl-M, boscalid, carboxin, fenhexamid, metalaxyl, metalaxyl-M, metsulfovax, ofurace, oxadixyl, oxycarboxin, pyracarbolid, thifluzamide or tiadinil; in particular benzanilide fungicides, such as benodanil, flutolanil, mebenil, mepronil, salicylanilide or tecloftalam; furanilide fungicides, such as fenfuram, furalaxyl, furcarbanil or methfuroxam; and sulfonanilide fungicides, such as flusulfamide; benzamide fungicides, such as benzohydroxamic acid, fluopicolide, tioxymid, trichlamide, zarilamid or zoxamide; furamide fungicides, such as cyclafuramid or furmecyclox; phenylsulfamide fungicides, such as dichlofluanid or tolylfluanid; sulfonamide fungicides, such as cyazofamid; and valinamide fungicides, such as benthiavalicarb or iprovalicarb; antibiotic fungicides, such as aureofungin, blasticidin-S, cycloheximide, griseofulvin, kasugamycin, natamycin, polyoxins, polyoxorim, streptomycin or validamycin; in particular strobilurin fungicides, such as azoxystrobin, dimoxystrobin, fluoxastrobin, kresoxim-methyl, metominostrobin, orysastrobin, picoxystrobin, pyraclostrobin or trifloxystrobin; aromatic fungicides, such as biphenyl, chlorodinitronaphthalene, chloroneb, chlorothalonil, cresol, dicloran, quintozene or tecnazene; benzimidazole fungicides, such as benomyl, carbendazim, chlorfenazole, cypendazole, debacarb, fuberidazole, mecarbinzid, rabenzazole or thiabendazole; benzimidazole precursor fungicides, such as furophanate, thiophanate or thiophanate-methyl; benzothiazole fungicides, such as bentaluron, chlobenthiazone or TCMTB; bridged diphenyl fungicides, such as bithionol, dichlorophen or diphenylamine; carbamate fungicides, such as benthiavalicarb, furophanate, iprovalicarb, propamocarb, thiophanate or thiophanate-methyl; in particular benzimidazolyl-carbamate fungicides, such as benomyl, carbendazim, cypendazole, debacarb or mecarbinzid; and carbanilate fungicides, such as diethofencarb; conazole fungicides; in particular imidazoles, such as climbazole, clotrimazole, imazalil, oxpoconazole, prochloraz or triflumizole; and triazoles, such as azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazol-cis, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole or uniconazole-P; copper fungicides, such as Bordeaux mixture, Burgundy mixture, Cheshunt mixture, copper acetate, copper carbonate, copper hydroxide, copper naphthenate, copper oleate, copper oxychloride, copper sulfate, copper zinc chromate, copper oxide, mancopper, cufraneb, cuprobam or oxine-copper; dicarboximide fungicides, such as famoxadone or fluoroimide; in particular dichlorophenyl carboximide fungicides, such as chlozolinate, dichlozoline, iprodione, isovaledione, myclozolin, procymidone or vinclozolin; and phthalimide fungicides, such as captafol, captan, ditalimfos, folpet or thiochlorfenphim; dinitrophenol fungicides, such as binapacryl, dinobuton, dinocap, dinocap-4, dinocap-6, dinocton, dinopenton, dinosulfon, dinoterbon or DNOC; dithiocarbamate fungicides, such as azithiram, carbamorph, cufraneb, cuprobam, disulfuram, ferbam, metam, nabam, tecoram, thiram or ziram; in particular cyclodithiocarbamate fungicides, such as dazomet, etem or milneb; and polymeric dithiocarbamate fungicides, such as mancopper, mancozeb, maneb, metiram, polycarbamate, propineb or zineb; imidazole fungicides, such as cyazofamid, fenamidone, fenapanil, glyodin, iprodione, isovaledione, pefurazoate or triazoxide; inorganic fungicides, such as potassium azide, sodium azide or sulfur; morpholine fungicides, such as, e.g., aldimorph, benzamorf, carbamorph, dimethomorph, dodemorph, fenpropimorph, flumorph or tridemorph; organophosphorus fungicides, such as ampropylfos, ditalimfos, edifenphos, fosetyl, hexylthiofos, iprobenfos, phosdiphen, pyrazophos, toiclofos-methyl or triamiphos; organotin fungicides, such as decafentin, fentin or tributyltin oxide; oxathiin fungicides, such as carboxin or oxycarboxin; oxazole fungicides, such as chlozolinate, dichlozoline, drazoxolon, famoxadone, hymexazol, metazoxolon, myclozolin, oxadixyl or vinclozolin; polysulfide fungicides, such as barium polysulfide, potassium polysulfide or sodium polysulfide; pyrazole fungicides, such as furametpyr or penthiopyrad; pyridine fungicides, such as boscalid, buthiobate, dipyrithione, fluazinam, fluopicolide, pyridinitril, pyrifenox, pyroxychloror pyroxyfur; pyrimidine fungicides, such as bupirimate, cyprodinil, diflumetorim, dimethirimol, ethirimol, fenarimol, ferimzone, mepanipyrim, nuarimol, pyrimethanil or triarimol; pyrrole fungicides, such as fenpiclonil, fludioxonil or fluoroimide; quinoline fungicides, such as ethoxyquin, halacrinate, 8-hydroxyquinoline sulfate, quinacetol or quinoxyfen; quinone fungicides, such as benquinox, chloranil, dichlone or dithianone; quinoxaline fungicides, such as quinomethionate, chlorquinox or thioquinox; thiazole fungicides, such as ethaboxam, etridiazole, metsulfovax, octhilinone, thiabendazole, thiadifluor or thifluzamide; thiocarbamate fungicides, such as methasulfocarb or prothiocarb; thiophene fungicides, such as ethaboxam or silthiofam; triazine fungicides, such as anilazine; triazole fungicides, such as bitertanol, fluotrimazole or triazbutil; urea fungicides, such as bentaluron, pencycuron or quinazamid; or unclassified fungicides, such as acibenzolar, acypetacs, allyl alcohol, benzalkonium chloride, benzamacril, bethoxazin, carvone, DBCP, dehydroacetic acid, diclomezine, diethyl pyrocarbonate, fenaminosulf, fenitropan, fenpropidin, formaldehyde, furfural, hexachlorbutadiene, isoprothiolane, methyl isothiocyanate, metrafenone, nitrostyrene, nitrothalisopropyl, OCH, phthalide, piperalin, probenazole, proquinazid, pyroquilon, sodium orthophenylphenoxide, spiroxamine, sultropen, thicyofen, tricyclazole or zinc naphthenate.

According to a particular embodiment of the invention, fungicides (e1) comprise:

1. acylalanines, such as benalaxyl, metalaxyl, ofurace or oxadixyl;
2. amine derivatives, such as aldimorph, dodine, dodemorph, fenpropimorph, fenpropidin, guazatine, iminoctadine, spiroxamine or tridemorph;
3. anilinopyrimidines, such as pyrimethanil, mepanipyrim or cyprodinil;
4. antibiotics, such as cycloheximide, griseofulvin, kasugamycin, natamycin, polyoxin and streptomycin;
5. azoles: azaconazole, bitertanol, bromoconazole, cyproconazole, diclobutrazol, difenoconazole, diniconazole, epoxiconazole, fenbuconazole, fluquinconazole, flusilazole, flutriafol, ketoconazole, hexaconazole, metconazole, myclobutanil, penconazole, propiconazole, prothioconazole, tebuconazole, tetraconazole, triadimefon, triadimenol, triflumizole or triticonazole;
6. dicarboximides, such as iprodione, myclozolin, procymidone or vinclozolin;
7. dithiocarbamates: ferbam, nabam, maneb, mancozeb, metam, metiram, propineb, polycarbamate, thiram, ziram or zineb;
8. heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophanate-methyl, tiadinil, tricyclazole or triforine;
9. nitrophenyl derivatives, such as binapacryl, dinocap, dinobuton or nitrothal-isopropyl;
10. phenylpyrroles, such as fenpiclonil and fludioxonil;
11. 2-methoxybenzophenones, such as disclosed in EP-A 897 904, e.g. metrafenone;
12. fungicides belonging to no other class, such as acibenzolar-5-methyl, benthiavalicarb, carpropamid, chlorothalonil, cyflufenamid, cymoxanil, diclomezine, diclocymet, diethofencarb, edifenphos, ethaboxam, fenhexamid, fentin acetate, fenoxanil, ferimzone, fluazinam, fosetyl, fosetyl-aluminum, iprovalicarb, metrafenone, pencycuron, propamocarb, phthalide, tolclofos-methyl, quintozene or zoxamide;
13. strobilurins, such as disclosed in WO 03/075663, e.g. azoxystrobin, dimoxystrobin, fluoxastrobin, kresoxim-methyl, metominostrobin, orysastrobin, picoxystrobin, pyraclostrobin and trifloxystrobin;

14. sulfonates, such as captafol, captan, dichlofluanid, folpet or tolylfluanid;
15. cinnamamides and their analogs, such as dimethomorph, flumetover or flumorph;
16. 6-aryl-[1,2,4]triazolo[1,5-a]pyrimidines, such as disclosed, e.g., in WO 98/46608, WO 99/41255 or WO 03/004465, e.g. 5-chloro-7-(4-methyl-piperidin-1-yl)-6-(2,4,6-trifluorophenyl)-[1,2,4]triazolo[1,5-a]pyrimidine, 5-chloro-7-(4-methylpiperazin-1-yl)-6-(2,4,6-trifluorophenyl)-[1,2,4]triazolo[1,5-a]pyrimidine, 5-chloro-7-(morpholin-1-yl)-6-(2,4,6-trifluorophenyl)-[1,2,4]triazolo[1,5-a]pyrimidine, 5-chloro-7-(piperidin-1-yl)-6-(2,4,6-trifluorophenyl)-[1,2,4]triazolo[1,5-a]pyrimidine, 5-chloro-7-(morpholin-1-yl)-6-(2,4,6-trifluorophenyl)-[1,2,4]triazolo[1,5-a]pyrimidine, 5-chloro-7-(isopropylamino)-6-(2,4,6-trifluorophenyl)-[1,2,4]triazolo[1,5-a]pyrimidine, 5-chloro-7-(cyclopentyl-amino)-6-(2,4,6-trifluorophenyl)-[1,2,4]triazolo[1,5-a]pyrimidine, 5-chloro-7-(2,2,2-trifluoroethylamino)-6-(2,4,6-trifluorophenyl)-[1,2,4]triazolo[1,5-a]pyrimidine, 5-chloro-7-(1,1,1-trifluoroprop-2-ylamino)-6-(2,4,6-trifluorophenyl)-[1,2,4]triazolo[1,5-a]pyrimidine, 5-chloro-7-(3,3-dimethylbut-2-ylamino)-6-(2,4,6-trifluorophenyl)-[1,2,4]triazolo[1,5-a]pyrimidine, 5-chloro-7-(cyclohexylmethyl)-6-(2,4,6-trifluorophenyl)-[1,2,4]triazolo[1,5-a]pyrimidine, 5-chloro-7-(cyclohexyl)-6-(2,4,6-trifluorophenyl)-[1,2,4]triazolo[1,5-a]pyrimidine, 5-chloro-7-(2-methylbut-3-yl)-6-(2,4,6-trifluorophenyl)-[1,2,4]triazolo[1,5-a]pyrimidine, 5-chloro-7-(3-methylprop-1-yl)-6-(2,4,6-trifluorophenyl)-[1,2,4]triazolo[1,5-a]pyrimidine, 5-chloro-7-(4-methylcyclohex-1-yl)-6-(2,4,6-trifluorophenyl)-[1,2,4]triazolo[1,5-a]pyrimidine, 5-chloro-7-(hex-3-yl)-6-(2,4,6-trifluorophenyl)[1,2,4]triazolo[1,5-a]pyrimidine, 5-chloro-7-(2-methylbut-1-yl)-6-(2,4,6-trifluorophenyl)-[1,2,4]triazolo[1,5-a]pyrimidine, 5-chloro-7-(3-methylbut-1-yl)-6-(2,4,6-trifluorophenyl)-[1,2,4]triazolo[1,5-a]pyrimidine, 5-chloro-7-(1-methylprop-1-yl)-6-(2,4,6-trifluorophenyl)-[1,2,4]triazolo[1,5-a]pyrimidine, 5-methyl-7-(4-methylpiperidin-1-yl)-6-(2,4,6-trifluorophenyl)-[1,2,4]triazolo[1,5-a]pyrimidine, 5-methyl-7-(4-methylpiperazin-1-yl)-6-(2,4,6-trifluorophenyl)-[1,2,4]triazolo[1,5-a]pyrimidine, 5-methyl-7-(morpholin-1-yl)-6-(2,4,6-trifluorophenyl)-[1,2,4]triazolo[1,5-a]pyrimidine, 5-methyl-7-(piperidin-1-yl)-6-(2,4,6-trifluorophenyl)-[1,2,4]triazolo[1,5-a]pyrimidine, 5-methyl-7-(morpholin-1-yl)-6-(2,4,6-trifluorophenyl)-[1,2,4]triazolo[1,5-a]pyrimidine, 5-methyl-7-(isopropylamino)-6-(2,4,6-trifluorophenyl)-[1,2,4]triazolo[1,5-a]pyrimidine, 5-methyl-7-(cyclopentylamino)-6-(2,4,6-trifluorophenyl)-[1,2,4]triazolo[1,5-a]pyrimidine, 5-methyl-7-(2,2,2-trifluoroethylamino)-6-(2,4,6-trifluorophenyl)-[1,2,4]triazolo[1,5-a]pyrimidine, 5-methyl-7-(1,1,1-trifluoroprop-2-ylamino)-6-(2,4,6-trifluorophenyl)-[1,2,4]triazolo[1,5-a]pyrimidine, 5-methyl-7-(3,3-dimethylbut-2-ylamino)-6-(2,4,6-trifluorophenyl)-[1,2,4]triazolo[1,5-a]pyrimidine, 5-methyl-7-(cyclohexylmethyl)-6-(2,4,6-trifluorophenyl)-[1,2,4]triazolo[1,5-a]pyrimidine, 5-methyl-7-(cyclohexyl)-6-(2,4,6-trifluorophenyl)-[1,2,4]triazolo[1,5-a]pyrimidine, 5-methyl-7-(2-methylbut-3-yl)-6-(2,4,6-trifluorophenyl)-[1,2,4]triazolo[1,5-a]pyrimidine, 5-methyl-7-(3-methylprop-1-yl)-6-(2,4,6-trifluorophenyl)-[1,2,4]triazolo[1,5-a]pyrimidine, 5-methyl-7-(4-methylcyclohex-1-yl)-6-(2,4,6-trifluorophenyl)-[1,2,4]triazolo[1,5-a]pyrimidine, 5-methyl-7-(hex-3-yl)-6-(2,4,6-trifluorophenyl)-[1,2,4]triazolo[1,5-a]pyrimidine, 5-methyl-7-(2-methylbut-1-yl)-6-(2,4,6-trifluorophenyl)-[1,2,4]triazolo[1,5-a]pyrimidine, 5-methyl-7-(3-methylbut-1-yl)-6-(2,4,6-trifluorophenyl)-[1,2,4]triazolo[1,5-a]pyrimidine and 5-methyl-7-(1-methylprop-1-yl)-6-(2,4,6-trifluorophenyl)-[1,2,4]triazolo[1,5-a]pyrimidine;
17. Amide fungicides, such as cyclofenamid, and (Z)—N-[α-(cyclopropylmethoxyimino)-2,3-difluoro-6-(difluoromethoxy)benzyl]-2-phenylacetamide.

Herbicides (e2) comprise, for example, amide herbicides, such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid or tebutam; in particular anilide herbicides, such as chloranocryl, cisanilide, clomeprop, cypromid, diflufenican, etobenzanid, fenasulam, flufenacet, flufenican, mefenacet, mefluidide, metamifop, monalide, napromide, pentanochlor, picolinafen or propanil; in particular arylalanine herbicides, such as benzoylprop, flamprop or flamprop-M; chloroacetanilide herbicides, such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchloror xylachlor; and sulfonanilide herbicides, such as benzofluor, cloransulam, diclosulam, florasulam, flumetsulam, metosulam, perfluidone, pyrimisulfan or profluazol; and sulfonamide herbicides, such as asulam, carbasulam, fenasulam, oryzalin or penoxsulam; antibiotic herbicides, such as bilanafos; aromatic acid herbicides; in particular benzoate herbicides, such as chloramben, dicamba, 2,3,6-TBA or tricamba; in particular pyrimidinyloxybenzoate herbicides, such as bispyribac or pyriminobac; and pyrimidinylthiobenzoate herbicides, such as pyrithiobac; phthalate herbicides, such as chlorthal; picolinate herbicides, such as aminopyralid, clopyralid or picloram; and quinolinecarboxylate herbicides, such as quinclorac or quinmerac; arsenical herbicides, such as cacodylat, CMA, DSMA, hexaflurate, MAA, MAMA, MSMA, potassium arsenite or sodium arsenite; benzoylcyclohexanedione herbicides, such as mesotrione or sulcotrione; benzofuranyl alkylsulfonate herbicides, such as benfuresate or ethofumesate; carbamate herbicides, such as asulam, carboxazole, chlorprocarb, dichlormate, fenasulam, karbutilate or terbucarb; carbanilate herbicides, such as barban, BCPC, carbasulam, carbetamide, CEPC, chlorbufam, chlorpropham, CPPC, desmedipham, phenisopham, phenmedipham, phenmedipham-ethyl, propham or swep; cyclohexene oxime herbicides, such as alloxydim, butroxydim, clethodim, cloproxydim, cycloxydim, profoxydim, sethoxydim, tepraloxydim or tralkoxydim; cyclopropylisoxazole herbicides, such as isoxachlortole or isoxaflutole; dicarboximide herbicides, such as benzfendizone, cinidon-ethyl, flumezin, flumiclorac, flumioxazin or flumipropyn; dinitroaniline herbicides, such as benfluralin, butralin, dinitramine, ethalfluralin, fluchloralin, isopropalin, methalpropalin, nitralin, oryzalin, pendimethalin, prodiamine, profluralin or trifluralin; dinitrophenol herbicides, such as dinofenate, dinoprop, dinosam, dinoseb, dinoterb, DNOC, etinofen or medinoterb; diphenyl ether herbicides, such as ethoxyfen; in particular nitrophenyl ether herbicides, such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen or oxyfluorfen; dithiocarbamate herbicides, such as dazomet or metam; halogenated aliphatic herbicides, such as alorac, chloropon, dalapon, flupropanate, hexachloroacetone, chloroacetic acid, SMA or TCA; imidazolinone herbicides, such as imazamethabenz, imazamox, imazapic, imazapyr, imazaquin or imazethapyr; inorganic herbicides, such as ammonium sulfamate, calcium chlorate, copper sulfate, iron sulfate, potassium azide, potassium cyanide, sodium azide, sodium chlorate or sulfuric acid; nitrile herbicides, such as bromobonil, bromoxynil, chloroxynil, dichlobenil, iodobonil, ioxynil or pyraclonil; organophosphorus herbicides, such as amiprofosmethyl, anilofos, bensulide, bilanafos, butamifos, 2,4-DEP, DMPA, EBEP, fosamine, glufosinate, glyphosate or piperophos; phenoxy herbicides, such as bromofenoxim, clomeprop, 2,4-DEB, 2,4-DEP, difenopenten, disul, erbon, etnipromid, fenteracol or trifopsime; in particular phenoxyacetic acid herbicides, such as 4-CPA, 2,4-D, 3,4-DA, MCPA or MCPA-thioethyl; phenoxybutyric acid herbicides, such as 4-CPB, 2,4-DB, 3,4-DB, MCPB or 2,4,5-TB; and phenoxypropionic acid herbicides, such as cloprop, 4-CPP, dichlorprop, dichlorprop-P, 3,4-DP, fenoprop, mecoprop or mecoprop-P; in particular aryloxyphenoxypropionic acid herbicides, such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P or trifop; phenylenediamine herbicides, such as dinitramine or prodiamine; phenyl pyrazolyl ketone herbicides, such as benzofenap, pyrazolynate, pyrazoxyfen or topramezone; pyrazolylphenyl herbicides, such as fluazolate or pyraflufen; pyridazine herbicides, such as credazine, pyridafol or pyridate; pyridazinone herbicides, such as brompyrazon, chloridazon, dimidazon, flufenpyr, metflurazon, norflurazon, oxapyrazon or pydanon; pyridine herbicides, such as aminopyralid, cliodinate, clopyralid, dithiopyr, fluoroxypyr, haloxydine, picloram, picolinafen, pyriclor, thiazopyr or triclopyr; pyrimidinediamine herbicides, such as iprymidam or tioclorim; quarternary ammonium herbicides, such as cyperquat, diethamquat, difenzoquat, diquat, morfamquat or paraquat; thiocarbamate herbicides, such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate or vernolate; thiocarbonate herbicides, such as dimexano, EXD or proxane; thiourea herbicides, such as methiuron; triazine herbicides, such as dipropetryn, triaziflam or trihydroxytriazine; in particular chlorotriazine herbicides, such as atrazine, chlorazine, cyanazine, cyprazine, eglinazine, ipazine, mesoprazine, procyazine, proglinazine, propazine, sebuthylazine, simazine, terbuthylazine or trietazine; methoxytriazine herbicides, such as atraton, methometon, prometon, secbumeton, simeton or terbumeton; and methylthiotriazine herbicides, such as ametryn, aziprotryne, cyanatryn, desmetryn, dimethametryn, methoprotryne, prometryn, simetryn or terbutryn; triazinone herbicides, such as ametridione, amibuzin, hexazinone, isomethiozin, metamitron or metribuzin; triazole herbicides, such as amitrole, cafenstrole, epronaz or flupoxam; triazolone herbicides, such as amicarbazone, carfentrazone, flucarbazone, propoxycarbazone or sulfentrazone; triazolopyrimidine herbicides, such as cloransulam, diclosulam, florasulam, flumetsulam, metosulam or penoxsulam; uracil herbicides, such as butafenacil, bromacil, flupropacil, isocil, lenacil or terbacil; urea herbicides, such as benzthiazuron, cumyluron, cycluron, dichloralurea, diflufenzopyr, isonoruron, isouron, methabenzthiazuron, monisouron or noruron; in particular phenylurea herbicides, such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, nebu-ron, parafluoron, phenobenzuron, siduron, tetrafluoron or thidiazuron; sulfonylurea herbicides; in particular pyrimidinylsulfonylurea herbicides, such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron or trifloxysulfuron; and triazinylsulfonylurea herbicides, such as chlorsulfuron, cinosulfuron, ethametsulfuron, iodosulfuron, metsulfuron, prosulfuron, thifensulfuron, triasulfuron, tribenuron, triflusulfuron or tritosulfuron; and thiadiazolylurea herbicides, such as buthiuron, ethidimuron, tebuthiuron, thiazafluoron or thidiazuron; and other herbicides, such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentoxazone, pinoxaden, prosulfalin, pyribenzoxim, pyriftalid, quinoclamine, rhodethanil, sulglycapin, thidiazimin, tridiphane, trimeturon, tripropindan or tritac.

According to a particular embodiment of the invention, herbicides (e2) comprise:

1. 1,3,4-thiadiazoles, such as buthidazole and cyprazole;
2. amides, such as allidochlor, benzoylprop-ethyl, bromobutide, chlorthiamid, dimepiperate, dimethenamid, diphenamid, etobenzanid, flamprop, flampropmethyl, fosamine, isoxaben, metazachlor, monalide, naptalam, pronamide, propanil, propyzamide or quinonamid;
3. aminotriazoles, such as amitrole,
4. anilides, such as anilofos, mefenacet or pentanochlor;
5. aryloxycarboxylic acids, such as 2,4-D, 2,4-DB, clomeprop, dichlorprop, dichlorprop-P, fenoprop, fluoroxypyr, MCPA, MCPB, mecoprop, mecoprop-P, napropamide, naproanilide or triclopyr;
6. benzoic acids, such as chloramben or dicamba;
7. benzothiadiazinones, such as bentazon;
8. bleachers, such as clomazone, diflufenican, fluorochloridone, flupoxam, fluridone, karbutilate, pyrazolate, sulcotrione or mesotrione;
9. carbamates, such as asulam, carbetamide, chlorbufam, chlorpropham, desmedipham, phenmedipham or vernolate;
10. quinolates, such as quinclorac or quinmerac;
11. dichloropropionic acids, such as dalapon;
12. dihydrobenzofurans, such as ethofumesate;
13. dihydrofuran-3-ones, such as flurtamone;
14. dinitroanilines, such as benefin, butralin, dinitramine, ethalfluralin, fluchloralin, isopropalin, nitralin, oryzalin, pendimethalin, prodiamine, profluralin or trifluralin;
15. dinitrophenols, such as bromofenoxim, dinoseb, dinoseb acetate, dinoterb, DNOC or minoterb-acetate;
16. diphenyl ethers, such as acifluorfen, acifluorfen-sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen or oxyfluorfen;
17. ureas, such as benzthiazuron, DCU, diflufenzopyr or methabenzthiazuron;
18. imidazolinones, such as imazamethapyr, imazapyr, imazaquin, imazethabenzmethyl, imazethapyr, imazapic or imazamox;

19. oxadiazoles, such as methazole, oxadiargyl, oxadiazon;
20. oxiranes, such as tridiphane;
21. phenols, such as bromoxynil or ioxynil;
22. phenoxyphenoxypropionic acid esters, such as clodinafop, cyhalofop-butyl, diclofop-methyl, fenoxaprop-ethyl, fenoxaprop-P-ethyl, fenthiaprop-ethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl;
23. phenylacetic acids, such as chlorfenac;
24. phenylureas, such as buturon, chlorotoluron, chlorbromuron, chloroxuron, dimefuron, diuron, fenuron, isoproturon, linuron, monolinuron, monuron, metobenzuron, metobromuron, metoxuron or neburon;
25. phenylpropionic acids, such as chlorfenprop-methyl;
26. Ppi-active compounds, such as benzofenap, flumiclorac, flumiclorac-pentyl, flumioxazin, flumipropyn, flupropacil, pyrazoxyfen, sulfentrazone or thidiazimin;
27. pyrazoles, such as nipyraclofen;
28. pyridazines, such as chloridazon, maleic hydrazide, norflurazon or pyridate;
29. pyridinecarboxylates, such as clopyralid, dithiopyr, picloram or thiazopyr;
30. pyrimidyl ethers, such as pyrithiobac, pyrithiobac-sodium, KIH-2023 or KIH-6127;
31. sulfonamides, such as flumetsulam or metosulam;
32. sulfonylureas, such as amidosulfuron, azimsulfuron, bensulfuron-methyl, chlorimuron-ethyl, chlorsulfuron, cinosulfuron, cyclosulfamuron, ethoxysulfuron, ethametsulfuron-methyl, flazasulfuron, flupyrsulfuron-methyl, foramsulfuron, halosulfuron-methyl, imazosulfuron, iodosulfuron, metsulfuron-methyl, nicosulfuron, oxasulfuron, primisulfuron, prosulfuron, pyrazosulfuron-ethyl, rimsulfuron, sulfometuron-methyl, sulfosulfuron, thifensulfuron-methyl, triasulfuron, tribenuron-methyl, triflusulfuron-methyl or tritosulfuron;
33. thiadiazolylureas, such as ethidimuron, tebuthiuron or thiazafluoron;
34. triazines, such as ametryn, atrazine, atraton, cyanazine, cyprazine, desmetryn, dipropetryn, isomethiozin, propazine, prometryn, prometon, sebuthylazine, secbumeton, simazine, terbutryn, terbumeton, terbuthylazine or trietazine;
35. triazolecarboxamides, such as triazofenamide;
36. uracils, such as bromacil, butafenacil, lenacil or terbacil;
37. furthermore azafenidin, aziprotryn, bromuron, benazolin, benfuresate, bensulide, benzofluor, bentazon, bromofenoxim, butamifos, cafenstrole, chlorthal-dimethyl, cinmethylin, cinidon-ethyl, defenuron, dichlobenil, endothall, fluorbentranil, fluthiacet-methyl, inxynil, isoxaflutole, mefluidide, methazole, metribuzin, metramitron, perfluidone, piperophos or topramezone;
38. plant protection agents of the cyclohexenone type, such as alloxydim, clethodim, cloproxydim, cycloxydim, sethoxydim and tralkoxydim.

Particularly preferred plant protection agents of the cyclohexanone type comprise tepraloxydim (cf. AGROW, No. 243, 11.3.95, p. 21, caloxydim) and 2-(1-[2-{4-chlorophenoxy}propyloxyimino]butyl)-3-hydroxy-5-(2H-tetrahydrothiopyran-3-yl)-2-cyclohexen-1-one, and a particularly preferred herbicidally active compound of the sulfonylurea type is N-(((4-methoxy-6-[trifluoromethyl]-1,3,5-triazin-2-yl)amino)-carbonyl)-2-(trifluoromethyl)benzenesulfonamide.

Insecticides (e3) comprise, for example, antibiotic insecticides, such as allosamidin or thuringiensin; in particular macrocyclic lactone insecticides, such as spinosad; in particular avermectin insecticides, such as abamectin, doramectin, emamectin, eprinomectin, ivermectin or selamectin; and milbemycin insecticides, such as lepimectin, milbemectin, milbemycinoxime or moxidectin; arsenical insecticides, such as calcium arsenate, copper acetoarsenite, copper arsenate, lead arsenate, potassium arsenite or sodium arsenite; botanical insecticides, such as anabasine, azadirachtin, d-limonene, nicotine, pyrethrins, cinerin E, cinerin I, cinerin II, jasmolin I, jasmolin II, pyrethrin I, pyrethrin II, quassia, rotenone, ryania or sabadilla; carbamate insecticides, such as bendiocarb or carbaryl; in particular benzofuranyl methylcarbamate insecticides, such as benfuracarb, carbofuran, carbosulfan, decarbofuran or furathiocarb; dimethylcarbamate insecticides, such as dimetan, dimetilan, hyquincarb or pirimicarb; oxime carbamate insecticides, such as alanycarb, aldicarb, aldoxycarb, butocarboxim, butoxycarboxim, methomyl, nitrilacarb, oxamyl, tazimcarb, thiocarboxime, thiodicarb or thiofanox; and phenyl methylcarbamate insecticides, such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC or xylylcarb; dinitrophenol insecticides, such as dinex, dinoprop, dinosam or DNOC; insect growth regulators; in particular chitin synthesis inhibitors, such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron or triflumuron; juvenile hormone mimics, such as epofenonane, fenoxycarb, hydroprene, kinoprene, methoprene, pyriproxyfen or triprene; juvenile hormones, such as juvenile hormone I, II and III; moulting hormone agonists, such as chromafenozide, halofenozide, methoxyfenozide, tebufenozide; moulting hormones, such as α-ecdysone or ecdysterone; moulting inhibitors, such as diofenolan; precocenes, such as precocene I, II and III; and unclassified insecticides, such as dicyclanil; nereistoxin analogs, such as bensultap, cartap, thiocyclam or thiosultap; nicotinoid insecticides, such as flonicamid; in particular nitroguanidine insecticides, such as clothianidin, dinotefuran, imidacloprid or thiamethoxam; nitromethylene insecticides, such as nitenpyram or nithiazine; and pyridylmethylamine insecticides, such as acetamiprid, imidacloprid, nitenpyram or thiacloprid; organochlorine insecticides, such as isobenzan, isodrin, kelevan or mirex; organophosphorus insecticides, in particular organophosphate insecticides, such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP or tetrachlorvinphos; organothiophosphate insecticides, such as dioxabenzofos, fosmethilan or phenthoate; in particular aliphatic organothiophosphate insecticides, such as acethion, amiton, cadusafos, chlorethoxyfos, chlormephos, demephion, demephion-O, demephion-S, demeton, demeton-O, demeton-S, demetonmethyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos or thiometon; in particular aliphatic amide organothiophosphate insecticides, such as amidithion, cyanthoate, dimethoate, ethoate-methyl, formothion, mecarbam, omethoate, prothoate, sophamide or vamidothion; and oxime organothiophosphate insecticides, such as chlorphoxim, phoxim or phoxim-methyl; heterocyclic organothiophosphate insecticides, such as azamethiphos, coumaphos, coumithoate, dioxathion, endothion, menazon, morphothion, phosalone, pyraclofos, pyridaphenthion or quinothion; especially benzothiopyran organothiophosphate insecticides, such as dithicrofos or thicrofos; benzotriazine organothiophosphate insecticides, such as azinphos-ethyl or azinphos-methyl; isoindole organothiophosphate insecticides, such as dialifos or phosmet; isoxazole organothiophosphate insecticides, such as isoxathion or zolaprofos; pyrazolopyrimidine organothiophosphate insecticides, such as chlorprazophos or pyrazophos; pyridine organothiophosphate insecticides, such as chlorpyrifos or chlorpyrifos-methyl; pyrimidine organothiophosphate insecticides, such as butathiofos, diazinon, etrimfos, lirimfos, pirimiphos-ethyl, pirimiphos-methyl, primidophos, pyrimitate or tebupirimfos; quinoxaline organothiophosphate insecticides, such as quinalphos or quinalphosmethyl; thiadiazole organothiophosphate insecticides, such as athidathion, lythidathion, methidathion or prothidathion; and triazole organothiophosphate insecticides, such as isazofos or triazophos; and phenyl organothiophosphate insecticides, such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 or trifenofos; phosphonate insecticides, such as butonate or trichlorfon; phosphonothioate insecticides, such as mecarphon; in particular phenyl ethylphosphonothioate insecticides, such as fonofos or trichloronat; and phenyl phenylphosphonothioate insecticides, such as cyanofenphos, EPN or leptophos; phosphoramidate insecticides, such as crufomate, fenamiphos, fosthietan, mephosfolan, phosfolan or pirimetaphos; phosphoramidothioate insecticides, such as acephate, isocarbophos, isofenphos, methamidophos and propetamphos; and phosphorodiamide insecticides, such as dimefox, mazidox, mipafox or schradan; oxadiazine insecticides, such as indoxacarb; phthalimide insecticides, such as dialifos, phosmet or tetramethrin; pyrazole insecticides, such as acetoprole, ethiprole, fipronil, pyrafluprole, pyriprole, tebufenpyrad, tolfenpyrad or vaniliprole; pyrethroid insecticides; in particular pyrethroid ester insecticides, such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alphacypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin or transfluthrin; and pyrethroid ether insecticides, such as etofenprox, flufenprox, halfenprox, protrifenbute or silafluofen; pyrimidinamine insecticides, such as flufenerim or pyrimidifen; pyrrole insecticides, such as chlorfenapyr; tetronic acid insecticides, such as spiromesifen; thiourea insecticides, such as diafenthiuron; urea insecticides, such as flucofuron or sulcofuron; or unclassified insecticides, such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene or triazamate.

According to a particular embodiment of the present invention, insecticides (e3) comprise:
1. organophosphates, such as azinphos-methyl, azinphos-ethyl, chlorpyrifos, chlorpyrifos-methyl, chlorfenvinphos, diazinon, dimethylvinphos, dioxabenzofos, disulfoton, ethion, EPN, fenitrothion, fenthion, heptenophos, isoxathion, malathion, methidathion, methyl parathion, paraoxon, parathion, phenthoate, phosalone, phosmet, phorate, phoxim, pirimiphos-methyl, profenofos, prothiofos, pirimiphos-ethyl, pyraclofos, pyridaphenthion, sulprofos, triazophos, trichlorfon, tetrachlorvinphos or vamidothion;
2. carbamates, such as alanycarb, benfuracarb, bendiocarb, carbaryl, carbofuran, carbosulfan, fenoxycarb, furathiocarb, indoxacarb, methiocarb, pirimicarb, propoxur, thiodicarb or triazamate;
3. pyrethroids, such as bifenthrin, cyfluthrin, cycloprothrin, cypermethrin, deltamethrin, esfenvalerate, etofenprox, fenpropathrin, fenvalerate, cyhalothrin, lambda-cyhalothrin, permethrin, silafluofen, tau-fluvalinate, tefluthrin, tralomethrin or alpha-cypermethrin;
4. arthropod growth regulators:
    A) chitin synthesis inhibitors, e.g. benzoylureas, such as chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole or clofentezine;
    B) ecdysone antagonists, such as halofenozide, methoxyfenozide or tebufenozide;
    C) juvenile hormone mimics, such as pyriproxyfen or methoprene;
    D) lipid biosynthesis inhibitors, such as spirodiclofen;
5. neonicotinoids, such as flonicamid, clothianidin, dinotefuran, imidacloprid, thiamethoxam, nithiazine, acetamiprid or thiacloprid;
6. additional insecticides which cannot be assigned to any of the abovementioned classes, such as abamectin, acequinocyl, acetamiprid, azadirachtin, bensultap, bifenazate, cartap, chlorfenapyr, diafenthiuron, dinotefuran, diofenolan, emamectin, ethiprole, fenazaquin, fipronil, hydramethylnon, imidacloprid, indoxacarb, isoprocarb, metolcarb, pyridaben, pymetrozine, spinosad, tebufenpyrad, thiamethoxam, XMC and xylylcarb, and
7. N-phenylsemicarbazones, such as disclosed in EP-A 462 456, in particular compounds of the general formula (IV)

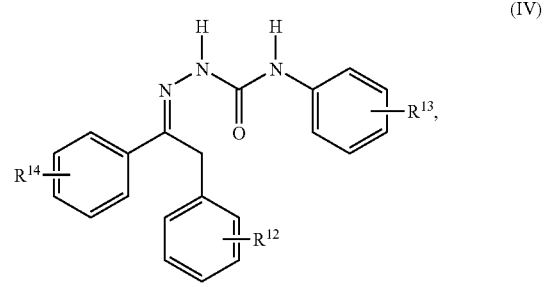

in which $R^{12}$ and $R^{14}$ can, independently of one another, be hydrogen, halogen, CN, $C_1$-$C_4$-alkyl, $C_1$-$C_4$-alkoxy, $C_{1-4}$-haloalkyl or $C_{1-4}$-haloalkoxy and $R^{13}$ is $C_{1-4}$-alkoxy, $C_{1-4}$-haloalkyl or $C_{1-4}$-haloalkoxy, e.g. compounds according to formula (IV) in which $R^{14}$=3-$CF_3$, $R^{12}$=4-CN and $R^{13}$=4-$OCF_3$.

Salts, in particular agriculturally useful salts, of the active agents especially mentioned here can also be used.

In a particular embodiment of the invention, the plant protection active agent is a fungicide.

In this context, it is particularly preferable for the fungicide to be an active agent from the group consisting of the strobilurins and triazoles, in particular a strobilurin chosen from azoxystrobin, pyraclostrobin, dimoxystrobin, trifloxystrobin, fluoxastrobin, picoxystrobin and orysastrobin or a triazole chosen from epoxiconazole, metconazole, tebuconazole, flusilazole, fluquinconazole, triticonazole, propiconazole, penconazole, cyproconazole and prothioconazole.

The use of epoxiconazole is particularly preferred according to the invention.

The names of plant protection active agents, e.g. epoxiconazole, chosen here include isomeric forms of these compounds. Mention may be made in particular of stereoisomers, such as enantiomers or diastereomers, of the formulae. In addition to the essentially pure isomers, the compounds of the formulae also include their isomeric mixtures, e.g. stereoisomeric mixtures.

Preference is generally given to active agents with a higher proportion of the stereoisomer which, with regard to the optical antipode, is biologically more active, particularly preferably isomerically pure active agents.

The proportion of the active agent component (e) in the total weight of the composition generally comes to more than 1% by weight, preferably more than 2% by weight and in particular more than 2.5% by weight. On the other hand, the proportion of the component (e) in the total weight of the composition generally comes to less than 50% by weight, preferably less than 40% by weight and in particular less than 35% by weight, based on the total weight of the composition.

In a particular embodiment of the invention, the composition is essentially anhydrous, in particular with a water content of less than 5% and especially of less than 2% of the total weight.

In a particular embodiment of the invention, the composition is of low hygroscopicity, it being preferable for its moisture absorption at 65% atmospheric humidity to be less than 20% by weight, preferably less than 15% by weight and particularly preferably less than 10% by weight.

In a particular embodiment of the invention, the composition is a particulate solid, in particular a granule or powder.

In this context, it is particularly preferable for the granule to be coarse-grained.

In this context, it is furthermore particularly preferable for the granule to be chosen from water-dispersible granules (WG) and water-soluble granules (SG), it being possible in particular for fluidized bed granules (FBG) to be concerned in this context.

In addition, it is particularly preferable for the powder to be a dry flowable (DF) powder, in particular a powder capable of being poured or trickled, particularly preferably again a powder with a particle size ranging from 1 to 200 µm, preferably ranging from 2 to 150 µm and in particular ranging from 5 to 100 µm, determined according to the CIPAC MT 59 method ("dry sieve test").

In a particular embodiment of the invention, the composition is essentially dust-free, determined according to the CIPAC MT 171 method ("dustiness of granular formulations").

In a particular embodiment of the invention, the composition is essentially stable on storage; in particular, it does not agglutinate on storage; in particular, it does not agglutinate on storage for at least eight weeks, preferably on storage for at least 12 weeks, at a temperature ranging from −10° C. to 40° C., determined according to the CIPAC MT 172 method ("flowability of water").

In a particular embodiment of the invention, the composition is dispersable in water, determined according to the CIPAC MT 174 method ("dispersibility of water dispersible granules").

An additional subject matter of the present invention is a process for the preparation of a solid plant protection composition according to the invention.

In this context,

FIG. 1 shows a diagrammatic representation of possible preparation routes.

In the practical preparation of the plant protection compositions according to the invention, use is generally made of commercial products which may yet additionally comprise solvents, for example water, and other additives, preferably high concentrates being used. In particular, relatively small amounts of inorganic substances, especially inorganic salts, may be included in the products used. Thus, relatively high molecular weight sulfonates may comprise, as a result of the preparation, up to 20% by weight of inorganic salts, in particular inorganic alkali metal salts, e.g. sodium sulfate. All amounts, such as percentages by weight and ratios by weight, in particular for the polyalkoxylates and relatively high molecular weight sulfonates according to the invention, are based according to the invention on the constituents mentioned by name and are to be converted on use of such commercial products in accordance with the actual content in the product of the constituents mentioned.

The solid plant protection composition can be prepared according to the invention by removing fluid from a fluid-comprising mixture comprising at least a portion of the ingredients and obtaining the solid at least partially freed from the fluid. The usual ingredients can, if need be, be introduced before removal of the fluid and/or can be added after removal of the fluid. In this context, the initial charge preferably ensues as solid. The admixture can ensue as fluid-comprising mixture, after which fluid is once again removed and the solid is obtained at least partially freed from the fluid. The fluid is preferably a solvent for one or more ingredients, in particular water. In the course of a multistage process, different fluids can also be used.

In a preferred embodiment, the fluid-comprising mixture comprises at least a portion of the components (a) and (b). Generally, it is even advisable for such a fluid-comprising mixture to comprise the total amount of the components (a) and (b). According to an additional preferred embodiment, the fluid-comprising mixture comprises at least a portion of the component (e). Generally, it is even advisable for such a fluid-comprising mixture to comprise the total amount of the component (e).

For the preparation of the solid plant protection compositions according to the invention, it is possible in principle to proceed such that (i) fluid is removed from a fluid-comprising mixture comprising components (a), (b) and (e); (ii) a solid comprising components (a) and (b), e.g. a solid comprising components (a) and (b) at least partially freed beforehand from the fluid, is introduced, a fluid-comprising mixture comprising component (e) is added and fluid is removed; or (iii) a solid comprising component (e), e.g. a solid comprising component (e) at least partially freed beforehand from the fluid, is introduced, a fluid-comprising mixture comprising components (a) and (b) is added and fluid is removed.

A solid comprising components (a) and (b) can be obtained, for example, by removing fluid from a fluid-comprising mixture comprising at least a portion of the components (a) and (b) and obtaining the solid at least partially freed from the fluid.

Preference is given, as solid comprising component (e), to powders or granules comprising at least 5% by weight, preferably at least 10% by weight and in particular at least 15% by weight of plant protection active agent. Such solids can be obtained, for example, by removing fluid from a fluid-comprising mixture comprising at least a portion of the component (e) and obtaining the solid at least partially freed from the fluid. In addition, mention may be made in this context in particular of common solid formulations of plant protection active agents, for example SGs, WGs, DFs or FBGs.

Preference is given, as fluid-comprising mixture at least of a portion of the component (e), to concentrates comprising at least 5% by weight, preferably at least 10% by weight and in particular at least 15% by weight of plant protection active agent. Mention may be made, in this context, in particular of common liquid formulations of plant protection active agents. Particular preference is given to the use of a liquid concentrate, in particular a single-phase concentrate, a multiphase concentrate, a suspension concentrate (SC) or a concentrate in the form of a suspoemulsion (SE). Furthermore, the addition is carried out particularly preferably by spraying, in particular in the fluidized-bed process, or by drum coating.

According to the invention, the composition is preferably prepared by the fastest possible removal of the fluid and thus in particular by the fastest possible drying, the processes which can be used being known in principle from the state of the art. The removal of fluid is described subsequently as "drying". In this context, what matters is that the removal of the fluid on local (molecular to supermolecular) size scales takes place quickly enough, which is beneficial to the formation of the solids according to the invention. The process as a whole can, on the other hand, if the feed materials optionally used allow this and practical considerations let this appear desirable, be carried out comparatively slowly, e.g. by sequential application of a relatively large number of very thin layers in the fluidized bed process, each of which for itself is quickly dried.

Fluid should according to the invention be withdrawn up to the or slightly above the point at which solids according to the invention are produced. A considerably more extensive removal of the fluid is possible in principle but not always advisable since an excessively low residual moisture content can, according to experience, harm the mechanical stability and dissolution properties of many granules ("destructive drying"); without being restricted to the theory, it is in this context assumed in principle that excessively great drying can result in undesirable rearrangement and crosslinking reactions in the granule. The ideal degree of drying for a particular process product is, because of the complexity of the system, dependent on many factors (including the properties desired and the use intended for the granule, the composition of the material charged, in the practical implementation of most favorable process variables, and the like) and is to be determined largely empirically.

According to a preferred embodiment of the invention, the removal of the fluid is carried out by convection drying. In this context, preference is given to processes in which the material to be dried is sprayed in fluid or pasty condition. This includes in particular spray drying, in which a fluid-comprising material is sprayed (feedstock), fluid is removed in the gas stream and the material, partially or completely freed from the fluid, is obtained as particulate outlet product. The spray processes also include fluidized-bed processes, in which a solid, preferably particulate, material is introduced ("initial charge"), a fluid-comprising material is sprayed ("feedstock"), fluid is removed in the gas stream, by which introduced particulate material and sprayed material are combined with one another, and the material, partially or completely freed from the fluid, is obtained in combination with the introduced particulate material as particulate "outlet product".

An additional suitable drying process is freeze drying (process C). This process is also familiar to a person skilled in the art.

The respective process product, generally the outlet product, can be used immediately according to the invention or, for its part, can be used as initial charge in additional processing stages for the preparation of the respective application form.

In a particular embodiment of the invention, the drying is carried out by spray drying, e.g. by use of a "spray tower" (process A).

In a specific embodiment of process A, compositions according to the invention, e.g. water-soluble granules (SGs), are prepared from the components (a), (b) and, if appropriate, (c) by spray-drying suitable fluid-comprising mixtures of (a), (b) and, if appropriate, (c), e.g. aqueous concentrates (process A1). In this context, the discharging of product is preferably carried out continuously.

In an additional specific embodiment of process A, compositions according to the invention, e.g. water-soluble granules (SGs) or dry flowable granules (DFs), are prepared from the components (a), (b) and, if appropriate, (c), as well as (e), by spray-drying fluid-comprising mixtures (of, e.g., aqueous concentrates) comprising (a), (b) and, if appropriate, (c), as well as (e) (process A2), the component (e) preferably being used in the form of concentrates, e.g. SL, SC or SE concentrates. In this context, the discharging of product is preferably carried out continuously.

If a component (b2) is used, this can thus be added technically as slurry or dispersion to the mixtures of the components (a), (b1) and, if appropriate, (c) before the spray drying ("co-spray-drying").

Ingredients which are assigned to the component (d) are in many cases introduced together with the standard components, for example in the form of commercial products.

In an additional particular embodiment of the invention, the drying is carried out in the fluidized bed process (process B).

In the fluidized bed process, the discharging of product is preferably carried out batchwise (batch process). For application of the process, it is generally necessary to introduce a suitable particulate material (carrier nuclei) by which the actual feedstock can then be taken up during the process. The feedstock can result from single- or multistream nozzle technology and/or bottom nozzles. Depending on installation for and control of the process, a single, a few or many layers can be applied to the nuclei, it being taken into account that each individual layer should dry quickly enough for the formation of the solids according to the invention to be beneficial. The choice of the number and thicknesses of the layers is, because of the complexity of the system, dependent on many factors (including, e.g., desired properties and use of the granule, composition of the material charged, in the practical implementation of most favorable process variables, and the like) and is to be determined largely empirically.

In a specific embodiment of process B, compositions according to the invention, e.g. water-soluble granules (SGs), are prepared by introducing particulate material (carrier nuclei) based on the component (d) and charging fluid-comprising mixtures (e.g. aqueous concentrates) comprising components (a), (b) and, if appropriate, (c) (process B1).

In an additional specific embodiment of process B, compositions according to the invention, in particular WGs, SGs or DFs, are prepared by introducing at least one solid comprising the components (a), (b) and, if appropriate, (c), generally a particulate solid, and subsequently charging one or more fluid-comprising mixtures (preferably in the form of concentrates, e.g. SL, SC or SE concentrates) comprising the component (e) and, if appropriate, additional portions of (c) (process B2). For the introduction of the initial charge, suitable particles can be prepared beforehand, e.g. by one of the processes A1, B1 or C.

In a particular embodiment of process B2, carrier nuclei based on the component (d) are introduced so that the material introduced comprises at least the components (a), (b), (d) and, if appropriate, (c).

In an additional specific embodiment of process B, compositions according to the invention, in particular WGs, SGs or DFs, are prepared by introducing carrier nuclei based on the component (d) and subsequently charging one or more fluid-comprising mixtures (e.g. aqueous concentrates) comprising at least the components (a), (b), (e) and/or, if appropriate, (c) (process B3).

In an additional specific embodiment of process B, compositions according to the invention, in particular WGs, SGs or DFs, are prepared by introducing a solid with effective plant protection activity, i.e. a solid comprising at least the component (e) and, if appropriate, (c), in particular a granule, e.g. available as outlet product from process B2, and charging one or more fluid-comprising mixtures (e.g. aqueous concentrates) comprising at least the components (a) and (b) and, if appropriate, additional portions of (c) (process B4).

Possible connections between the individual process sequences of the preferred embodiments of processes A and B are represented, for example, in FIG. 1. Of course, other processes, e.g. C, can also serve as source for the particles introduced, e.g., in process B2. If desired, more complex sequences than those represented in the general view are also possible (e.g. coating of particles comprising carrier and active agent, prepared according to A2, with an additional layer, likewise comprising carrier and active agent, in B2), which may be suitable, e.g., for the preparation of a combination of several active agents which are poorly compatible with one another (e.g. different strongly acidic and strongly basic substances or substances which can potentially react with one another) and/or for granules with specific properties (e.g. an extent of storage stability under extreme climatic conditions beyond that according to the present invention).

In this way, solid plant protection compositions, in particular coarse plant protection composition granules, are obtained which can be dispersed (water-dispersible granules) or dissolved (water-soluble granules) in stable aqueous active agent preparations and moreover do not give off dust. The solid plant protection compositions thus obtained are stable on storage.

An additional subject matter of the present invention is accordingly the pesticidal, in particular fungicidal, insecticidal or herbicidal, treatment of plants and their habitats with a plant protection composition according to the invention or the use of the disclosed plant protection compositions for the pesticidal, in particular fungicidal, insecticidal or herbicidal, treatment of plants and their habitats.

For this, the solid plant protection compositions according to the invention, before they are used, are generally converted by the user, e.g. the farmer or gardener, in a way essentially known, by dissolving, dispersing or emulsifying in water, to a ready-for-application application form, e.g. treated to give a spray mixture (tank mix method).

The spray mixture prepared can be applied in a generally known way in the spray method, especially by spraying, for instance, with a mobile spraying device from nozzles which distribute as finely as possible. Furthermore, the usual devices and working techniques for this are known to a person skilled in the art.

According to a particular embodiment, the treatment of plants and their habitats is accordingly carried out in the spray method. In this context, it is preferable for the preparation of the spray mixture to be applied to be carried out by dissolving, dispersing or emulsifying and particularly preferable again for the dissolving, dispersing or emulsifying to be carried out in the tank mix method.

An additional subject matter of the present invention is a spray mixture comprising a plant protection composition according to the invention for the pesticidal treatment of plants.

In a particular embodiment of the invention, the spray mixture comprises from 0.0001 to 10% by weight, preferably from 0.001 to 1% by weight and in particular from 0.01 to 0.5% by weight of plant protection active agent. This corresponds to approximately from 0.01 to 5% by weight, preferably from 0.05 to 3% by weight and in particular from 0.1 to 2% by weight of plant protection composition according to the invention.

The present invention will now be more fully described using the following examples, which are not to be regarded as limiting.

REFERENCE EXAMPLES 1 TO 37

Polyalkoxylate-Comprising Solids

A series of polyalkoxylate-comprising solids was prepared according to processes V1, V2, V3 or V4 and evaluated.

Process V1: Preparation by Means of Freeze Drying

The respective ingredients were treated with water and dissolved in a 250 ml round-bottomed flask with stirring at RT or with gentle heating at 50° C. Subsequently, the round-bottomed flask was placed in an acetone/dry ice bath and the mixture was frozen at approximately from −70 to −78° C. to give a solid mass. Alternatively, liquid nitrogen or liquid air was used for the freezing. The freezing generally lasted only a few minutes.

The flask was then connected to a conventional freeze drying apparatus. Depending on amount, the freeze drying process lasted up to 48 hours, a partial vacuum of less than 0.5 mbar typically being installed.

The residues were isolated from the flasks, i.e. generally scraped out with a spatula, and subsequently evaluated in their properties.

Process V2: Preparation by Means of Evaporation

The ingredients are dissolved in water and a portion of this amount is placed in a petri dish in a layer depth of ca. 1-2 mm. The petri dish is, up to constant weight, placed on a hot plate and the aqueous mixture is dried at 100° C. by free evaporation of water at atmospheric pressure.

Process V3: Preparation by Means of Rotary Evaporation

The ingredients are dissolved in water and evaporated on a rotary evaporator at 60° C. and 100 down to ca. 50 mbar.

The details with regard to ingredients, amounts, preparation process and evaluation for some formulations are collated in the following table 1.

TABLE 1

| Ref. Ex. | Ingredients (proportions in g) | Aqueous mixture | Process | Consistency[1] | Hygroscopicity[2] |
|---|---|---|---|---|---|
| 1a | (60) Urea<br>(40) W. LF 700 | 400 g[3] | V1 | S-3 | |
| 1b | (50) W. LF 700<br>(50) Wettol D 1 | 150 g[3] | V1 | S-1 | 10.7% (65%) |
| 1c | (10) Urea<br>(40) Wettol D 1<br>(50) W. LF 700 | 150 g[3] | V1 | S-1 | 7.1% (65%) |
| 2 | (3) W. LF 700<br>(4) Adinol OT<br>(3) Urea | 100 g[3] | V1 | S-3 | |
| 3 | (5) W. LF 700<br>(1) Wettol D 1<br>(4) Urea | 100 g[3] | V1 | S-2 | |
| 4 | (5) W. LF 700<br>(2) Wettol D 1<br>(3) Urea | 100 g[3] | V1 | S-0/S-1 | |
| 5 | (2.1) W. LF 700<br>(2.9) Adinol OT<br>(5) Urea | 100 g[3] | V1 | S-1 | 31.6% (65%) |
| 6 | (5) W. LF 700<br>(2) Tamol NH 7519<br>(3) Urea | 100 g[3] | V1 | S-1 | 8.24% (65%) |
| 7 | (50) W. LF 700<br>(20) Sipernat 22<br>(30) Urea | 100 g[3] | V1 | S-3 | 2.94% (65%) |
| 8 | (50%) Wettol D 1<br>(45%) W. LF 700<br>(5%) Sipernat 50 S | 50 g/150 g[4] | V1 | S-0 to S-1 | |
| 9 | (50%) Wettol D 1<br>(40%) W. LF 700<br>(10%) Sipernat 50S | 50 g/150 g[4] | V1 | S-0 to S-1 | 7.4% (65%) |
| 10 | (45%) Wettol D 1<br>(35%) W. LF 700<br>(20%) Sipernat 50S | 50 g/150 ml[4] | V1 | S-1 | |
| 11 | (50%) W. LF 700<br>(50%) Tamol NH7519 | 20 g/80 ml[4] | V1 | S-0 to S-1 | 9.84% (65%) |
| 12 | (50%) W. LF 700<br>(50%) Ufoxane 3 A<br>(Starting solution somewhat hazy) | 20 g/80 ml[4] | V1 | S-0 to S-1 | 12.81% (65%) |
| 13a | (10 g) W. LF 700<br>(6.6 g) Ufoxane 3 A<br>(3.3 g) Tamol NH 7519 | 20 g/80 ml[4] | V1 | S-0 | 6.6% (50%) |
| 13b | (6 g) W. LF 700<br>(6.7 g) Ufoxane 3 A<br>(3.3 g) Tamol NH7519<br>(4.0 g) Aerosol OTA | In 80 ml[5] | V1 | S-1 | |
| 14a | (5 g) W. LF 700<br>(5 g) Klearfax AA 270<br>(10 g) Wettol D 1 | In 80 ml[5] | V1 | S-0 | 7.5% (50%) |
| 14b | (8 g) W. LF 700<br>(2 g) Pluronic PE 6800<br>(3.33 g) Tamol NH7519<br>(6.66 g) Ufoxane 3 A | In 80 ml[5] | V1 | S-0 to S-1 | |
| 15 | (50%) W. LF 700<br>(50%) Lutensit A-LBN | 20 g/160 ml[4] | V1 | S-4 | |
| 16 | (40%) W. LF 700<br>(10%) Ammonium sulfate<br>(50%) Urea | In 80 ml[5] | V1 | S-3 | |
| 17 | (10 g) Tamol NH 7519<br>(10 g) W. LF 700 | 20 g/180 g[4] | V2 | S-4 | |
| 18 | (10 g) Tamol NH 7519<br>(10 g) W. LF 700 | 20 g/180 g[4] | V3 | S-4 | |
| 19 | (50%) Wettol D 1<br>(50%) Cremophor EL | 20 g/80 ml[4] | V1 | S-1-S-2 | 4.5% (50%)<br>7.7% (65%) |
| 20 | (33.3%) Ufoxane 3A<br>(50%) Cremophor EL<br>(16.7%) Tamol NH 7519 | 20 g/80 ml[4] | V1 | S-1 | 7.3% (50%)<br>13.2% (65%) |
| 21 | (50%) Wettol D 1<br>(50%) Lutensol AO3 | 20 g/80 ml[4] | V1 | S-1 to S-2 | 4.0% (50%)<br>7.0% (65%) |
| 22 | (33.3%) Ufoxane 3A<br>(50%) Lutensol AO3<br>(16.7%) Tamol NH 7519 | 20 g/80 ml[4] | V1 | S-0 | 7.1% (50%)<br>13.1% (65%) |
| 23 | (6.7 g) Ufoxane 3A<br>(4.5 g) Synperonic 10/7<br>(5.5 g) Synperonic 10/11<br>(3.3 g) Tamol NH 7519 | 20 g/80 ml[4] | V1 | S-0 | 7.5% (50%)<br>13.9% (65%) |

TABLE 1-continued

| Ref. Ex. | Ingredients (proportions in g) | Aqueous mixture | Process | Consistency[1] | Hygroscopicity[2] |
|---|---|---|---|---|---|
| 24 | (10 g) Wettol D 1<br>(4.5 g) Synperonic 10/7<br>(5.5 g) Synperonic 10/11 | 20 g/80 ml[4] | V1 | S-1 | 4.3% (50%)<br>7.9% (65%) |
| 25 | (50 g) Lutensol TO8<br>(50 g) Wettol D 1 | 20 g/80 ml[4] | V1 | S-1 to S-2 | 4.6% (50%)<br>8.2% (65%) |
| 26 | (50 g) Lutensol ON 30<br>(50 g) Wettol D 1 | 20 g/80 ml[4] | V1 | S-1 | 4.3% (50%)<br>8.0% (65%) |
| 27 | (50 g) Lutensol ON 30<br>(33.3 g) Ufoxane 3A<br>(16.7 g) Tamol NH 7519 | 20 g/80 ml[4] | V1 | S-0 | 7.5% (50%)<br>14.1% (65%) |
| 28 | (50 g) Lutensol A 8<br>(50 g) Wettol D 1 | 20 g/80 ml[4] | V1 | S-0 | 4.6% (50%)<br>8.0% (65%) |
| 29a | (50 g) Lutensol A 8<br>(33.3 g) Ufoxane 3A<br>(16.7 g) Tamol NH 7519 | 20 g/80 ml[4] | V1 | S-0 | 7.2% (50%)<br>13.5% (65%) |
| 29b | (50 g) Lutensol AO 10<br>(33.3 g) Ufoxane 3A<br>(16.7 g) Tamol NH 7519 | 20 g/80 ml[4] | V1 | S-1 | 7.6% (50%)<br>13.8% (65%) |
| 30 | (50 g) Glycerox HE<br>(50 g) Wettol D 1 | 20 g/80 ml[4] | V1 | S-0 | 4.2% (50%)<br>7.8% (65%) |
| 31 | (50 g) Glycerox HE<br>(33.3 g) Ufoxane 3A<br>(16.7 g) Tamol NH 7519 | 20 g/80 ml[4] | V1 | S-0 | 7.5% (50%)<br>14.2% (65%) |
| 32 | (50 g) Castor oil-20 EO<br>(50 g) Wettol D 1 | 20 g/80 ml[4] | V1 | S-1 | |

[1]Evaluations of the consistency:
S-0: good properties, solid powder which, on scratching or rubbing with a spatula, remains solid and friable and shows no tendency to smear.
S-1: shows virtually no smearing on scratching with the spatula;
S-2: shows very slight smearing on scratching with the spatula;
S-3: clearly shows smearing under mechanical stress or on scratching;
S-4: the freeze-dried mass is already viscous and shows considerable smearing;
[2]Hygroscopicity given in % by weight of moisture absorption at a relative humidity value of 50% or 65% (the determination was carried out in each case up to the saturation value, i.e. constant weight, the increase in weight of 1 g samples in small petri dishes being determined up to 4 weeks)
[3]Total amount of the ingredients dissolved in water
[4]Amount of ingredient/amount of water
[5]Amount of water in which the ingredients were dissolved Process A4: Preparation by Means of Spray Drying The ingredients were dissolved in water and spray dried in a spray tower from Niro-Reiholb (disk tower; height: 6 m; diameter: 1 m; two-fluid nozzle with circulating gas unit, cyclone and filter system; use of nitrogen; nozzle gas mass flow rate: 11.5 kg/h; nozzle gas admission pressure: 2.7 bar; product inlet temperature: 20° C.) under the conditions mentioned in the following table 2.

TABLE 2

| Ex. | Batch/Components | Gas inlet temp. (° C.) | Gas outlet temp. (° C.) | Gas mass flow rate (kg/h) | Throughput (kg/h) (spray amount) |
|---|---|---|---|---|---|
| 33 | 200 kg Water<br>50 kg Wettol D 1<br>50 kg Wettol LF 700 | 162 | 79 | 460 | 22 |
| 34 | 60 kg Water<br>15 kg Wettol D 1<br>10 kg Wettol LF 700 | 162 | 84 | 490 | 19 |
| 35***) | 30 kg Water<br>20 kg Tamol NLP<br>10 kg Wettol LF 700 | 154 | 84 | 500 | 18 |
| 36 | 40 kg Water<br>10 kg Ufoxane 3A<br>10 kg Wettol LF 700 | 162 | 83 | 510 | 20 |
| 37 | 40 kg Water<br>10 kg Tamol NH 7519<br>10 kg Wettol LF 700 | 123 | 77 | 500 | 12 |

***)Invalid test; no discharge of product; ca. 50 kg of powder in the filter.

The residual moisture contents of the solid formulations obtained were 2.1% (example 33), 1.7% (example 34) or 1.5% (example 36).

The following table 3 is a digest of the ingredients used.

TABLE 3

| Name | Correspondence | Additional description | Manufacturer |
|---|---|---|---|
| Wettol D 1 | Sulfonate of the formula III | Sodium salt, cf. EP 707 445 | BASF AG |
| Wettol LF 700 | Alkoxylate of the formula I | $C_{12}$-$C_{14}$-fatty alcohol × PO/EO, cf. EP 707 445; | BASF AG |
| Sipernat 22 | Inorganic solid | Silicon dioxide product | Degussa |
| Sipernat 50S | Inorganic solid | Silicon dioxide product | Degussa |
| Tamol NH 7519 | Sulfonate of the formula II | Naphthalenesulfonic acid-formaldehyde polycondensate, sodium salt | BASF AG |
| Ufoxane 3A | Sulfonate | Lignosulfonate | |
| Lutensit A-LBN | — | Dodecylbenzenesulfonic acid, sodium salt | BASF AG |
| Aerosol OTA | Additional auxiliary | | |
| Cremophor EL | Alkoxylate of the formula I | Polyglycol ricinoleate | BASF AG |
| Tamol NLP* | Sulfonate of the formula II | Naphthalenesulfonic acid-formaldehyde polycondensate, ammonium salt | BASF AG |
| Silicon SRE | Additional auxiliary | Antifoaming agent | Wacker |
| Lutensol AO3 | Alkoxylate of the formula I | $C_{13}$-$C_{15}$-fatty alcohol × EO | BASF AG |
| Klearfax AA 270 | Alkoxylate of the formula I | Phosphate ester of a polyalkoxylated fatty alcohol; CAS No.: 68649-29-6 | BASF Corp., US |
| Pluronic PE 6800 | — | PO/EO block polymer | BASF AG |
| Synperonic 10/7 | Alkoxylate of the formula I | Fatty alcohol-EO | Uniqema |
| Synperonic 10/11 | Alkoxylate of the formula I | Fatty alcohol × EO | Uniqema |
| Lutensol TO8 | Alkoxylate of the formula I | Iso-$C_{13}$-alcohol × EO | BASF AG |
| Lutensol ON 30 | Alkoxylate of the formula I | Iso-$C_{10}$-Alkohol × EO | BASF AG |
| Lutensol A 8 | Alkoxylate of the formula I | $C_{12}$-$C_{14}$-Alcohol × EO | BASF AG |
| Lutensol AO 10 | Alkoxylate of the formula I | $C_{13}$-$C_{15}$-Alcohol × EO | BASF AG |
| Castor oil-20 EO | Alkoxylate of the formula I | Castor oil × 20 EO | |
| Glycerox HE | Alkoxylate of the formula I | Ethoxylated glyceryl cocoate; commercial product with the CAS No. 68553-03-7 | Croda Ltd., GB |

Without being committed to the theory, the following mechanism is proposed to explain the observation that relatively high molecular weight sulfonates with high and, as a percentage by weight, identical or similar proportions of polyalkoxylates produce solid powders on spray drying or on freeze drying;

In both cases, both in spray drying and in freeze drying, the solvent, generally water, is quickly and/or relatively gently removed from the preconcentrates. In this context, it can be assumed that, first, associates are present or are formed, characterized in that, in addition to dipole-dipole and Van der Waals interactions, "template" effects (i.e., favoring and/or changing the incorporation of macromolecules in preformed supermolecular aggregations as a result of cooperative effects, similar to the processes known in the formation of many biological macromolecular structures) also play a role, in which the cation of the sulfonate interacts with the polyalkoxylate chain with formation of chelate-like structures. In this way, poly- or macromeric cations and poly- or macromeric anions with comparatively high stability are produced.

It is known in general that large and/or macromeric unstable anions with many degrees of freedom of the orientation in space, i.e. low rigidity of the molecule, can in many cases form stable lattices or solids with crystalline structure and/or associates with melting points of greater than 50° C. only with likewise large and/or macromeric cations. On microscopic inspection, these backbone associates survive on fast or gentle, kinetically controlled removal of solvent according to the invention. Macroscopically, this operation in the end produces loose powders or granules, typically with proportions of air of at least 20% by volume and bulk densities between 0.3 and 0.9 g/ml.

In contrast to this, the slow or nongentle removal of the solvent from mixtures according to the invention, as takes place, e.g., in a rotary evaporator, leads, with disintegration of the molecular associates under thermodynamic control, to

EXAMPLES 1 AND 2

Plant Protection Compositions Based on Epoxiconazole

Two plant protection compositions based on an epoxiconazole suspension concentrate (epoxiconazole SC) were prepared according to process V4 or V5 and evaluated.

Epoxiconazole SC:

1.5 kg of SC were prepared according to EP 707 445 B1 by milling, in a laboratory bead mill, an aqueous mixture with 12.5% of epoxiconazole, 5% of Wettol LF 700, 2.5% of Tamol NH 7519 and 0.1% of Silicon SRE (antifoaming agent), a particle size distribution of 80%<2 μm being obtained.

Example 1

The ingredients were dissolved in water and spray dried according to process V4.

| Ex. | Batch/Components | Gas inlet temp. (° C.) | Gas outlet temp. (° C.) | Gas mass flow rate (kg/h) | Throughput (kg/h) (spray amount) |
|---|---|---|---|---|---|
| 1 | 60 kg Water<br>5.6 kg Wettol D 1<br>5.6 kg Wettol LF 700<br>4 kg Epoxiconazole SC | 115 | 75 | 500 | 9 |

Example 2

Process V5: Preparation by Means of a Fluidized Bed

An FBG laboratory unit (Turbojet model) from Hüttlin is fluidized at 70° C. with ca. 80 m³ of nitrogen stream with 1.5 kg of the mixture from example 33. 2.5 kg of epoxiconazole SC are then sprayed on within 45 minutes via the three bottom nozzles of the unit, a coarse-grained granule with good dispersing properties being obtained. The granule output, calculated at 2.0 kg, was actually ca. 1.9 kg, with a proportion of active agent of approximately 19% of epoxiconazole and a proportion of polyalkoxylate (Wettol LF 700) of 38%.

The plant protection compositions according to the invention are dust-free, quickly wettable, readily dispersible and nonhygroscopic or only slightly hygroscopic granules with good storage stability.

We claim:

1. A solid plant protection composition comprising:
   a) liquid or low melting point polyalkoxylate having a melting point of less than 40° C.;
   b) a carrier comprising a relatively high molecular weight sulfonate having a weight-average molecular weight of at least one kDa; and
   e) a plant protection active agent,
   wherein
   i) the weight ratio of the liquid or low melting point polyalkoxylate to the plant protection active agent is at least 1:2 and the proportion of the liquid or low melting point polyalkoxylate, based on the total weight of the composition, is at least 15% by weight;
   ii) the proportion of the liquid or low melting point polyalkoxylate, based on the total weight of the relatively high molecular weight sulfonate, is at least 30% by weight; and
   iii) the weight ratio of the liquid or low melting point polyalkoxylate to the relatively high molecular weight sulfonate is at most 3:1.

2. The composition according to claim 1, comprising from 1 to 50% by weight of the plant protection active agent.

3. The composition according to claim 1, wherein the plant protection active agent is chosen from fungicidal active agents from the triazoles series and active agents from the strobilurins series.

4. The composition according to claim 1, wherein the polyalkoxylate is chosen from optionally end-group-modified alkoxylated fatty alcohols, alkoxylated fatty acid esters, alkoxylated fatty amines, alkoxylated glycerides, alkoxylated sorbitan esters, alkoxylated alkylphenols, alkoxylated distyrylphenols, and alkoxylated tristyrylphenols.

5. The composition according to claim 1, wherein the polyalkoxylate is chosen from alcohol polyalkoxylates of the formula (I)

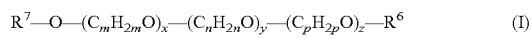

$$R^7-O-(C_mH_{2m}O)_x-(C_nH_{2n}O)_y-(C_pH_{2p}O)_z-R^6 \qquad (I)$$

in which $R^6$ is hydrogen, alkyl, alkenyl, acyl, aryl, or an inorganic acid group;

$R^7$ is an aliphatic hydrocarbon radical with from 3 to 100 carbon atoms;

m, n and p are, independently of one another, a whole number from 2 to 6;

x, y and z are, independently of one another, a number from 0 to 1000; and x+y+z corresponds to a value from 2 to 1000.

6. The composition according to claim 5, wherein $R^7$ is branched or linear $C_{3-30}$-alkyl.

7. The composition according to claim 1, comprising at least 20% by weight of the polyalkoxylate.

8. The composition according to claim 1, comprising at most 60% by weight of the polyalkoxylate.

9. The composition according to claim 1, wherein the relatively high molecular weight sulfonate exhibits a weight-average molecular weight of at least 5 kDa.

10. The composition according to claim 1, wherein the relatively high molecular weight sulfonate is a lignosulfonate.

11. The composition according to claim 1, wherein the relatively high molecular weight sulfonate is a condensation product based on a sulfonated aromatic compound, an aldehyde and/or a ketone.

12. The composition according to claim 11, wherein the condensation product comprises repeat units with the structure of the formula (IIa)

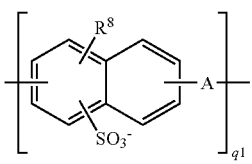
(IIa)

and/or formula (IIb)

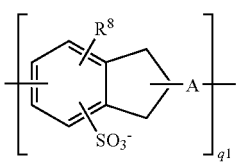
(IIb)

and/or formula (IIc)

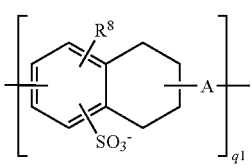
(IIc)

in which

R$^8$ is hydrogen, one or more hydroxyl groups or one or more C$_{1-8}$-alkyl radicals;

q1 corresponds to a value of at least 100; and

A is methylene, 1,1-ethylene or a group of the formulae

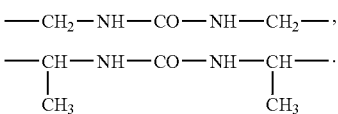

13. The composition according to claim 11, wherein the condensation product comprises repeat units with the structure of the formula (III):

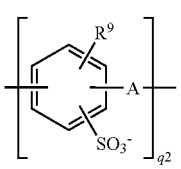
(III)

in which

R$^9$ is hydrogen, one or more hydroxyl groups or one or more C$_{1-8}$-alkyl radicals;

q2 corresponds to a value of at least 100 to 10$^{10}$; and

A is methylene, 1,1-ethylene or a group of the formulae

-continued $$-\text{CH}-\text{NH}-\text{CO}-\text{NH}-\text{CH}-$$
$$\phantom{-}\text{CH}_3 \phantom{-\text{NH}-\text{CO}-\text{NH}-}\text{CH}_3$$

14. The composition according to claim 1, wherein the relatively high molecular weight sulfonate is a copolymer, the constituent monomers M of which comprise
α) at least one monoethylenically unsaturated monomer M1 exhibiting at least one sulfonic acid group, and
β) at least one neutral monoethylenically unsaturated monomer M2.

15. The composition according to claim 1, wherein the relatively high molecular weight sulfonate is an ammonium, alkali metal, alkaline earth metal or transition metal sulfonate.

16. The composition according to claim 1, comprising at least 15% by weight of the relatively high molecular weight sulfonate.

17. The composition according to claim 1, comprising at most 70% by weight of the relatively high molecular weight sulfonate.

18. The composition according to claim 1, wherein the weight ratio of the liquid or low melting point polyalkoxylate to the relatively high molecular weight sulfonate is at most 2:1.

19. The composition according to claim 1, wherein the weight ratio of the liquid or low melting point polyalkoxylate to the relatively high molecular weight sulfonate is at least 4:3.

20. The composition according to claim 1, wherein the component (b) comprises the relatively high molecular weight sulfonate as component (b1); and an inorganic solid as component (b2).

21. The composition according to claim 20, wherein the inorganic solid is sparingly soluble or insoluble in water, wherein at least 100 parts of water are necessary to dissolve one part of inorganic solid at 20° C.

22. The composition according to claim 20, wherein the inorganic solid is chosen from aluminium oxide, bauxite, silicates and silicate minerals, diatomaceous earths, silicas, pyrophylite, talc, mica and clays.

23. The composition according to claim 22, wherein the proportion of inorganic solid therein altogether is less than 15% by weight.

24. The composition according to claim 20, wherein the weight ratio of the relatively high molecular weight sulfonate to the inorganic solid is at least 2.

25. The composition according to claim 1, furthermore comprising:
c) an additional auxiliary.

26. The composition according to claim 25, wherein the additional auxiliary is chosen from
c1) surface-active auxiliaries;
c2) suspension agents, antifoaming agents, retention agents, pH buffers, drift retardants and other auxiliaries for improving the handleability and/or physical properties of the formulation; and
c3) chelating agents.

27. The composition according to claim 25, comprising at most 60% by weight of the additional auxiliary.

28. The composition according to claim 1, furthermore comprising:
d) a water-soluble inorganic salt.

29. The composition according to claim 28, wherein the inorganic salt is ammonium sulfate.

30. The composition according to claim 1, which is essentially anhydrous with a water content of less than 5% of the total weight.

31. The composition according to claim 1, in the form of granules.

32. The composition according to claim 31, wherein the granules are water-dispersible granules or water-soluble granules.

33. The composition according to claim 31, wherein the granules are fluidized-bed granules.

34. The composition according to claim 1, in the form of a powder.

35. The composition according to claim 34, wherein the powder is a dry flowable powder.

36. A process for the preparation of a composition according to claim 1, wherein fluid is removed from a fluid-comprising mixture comprising at least a portion of components (a), (b) and (e) and the solid is obtained at least partially freed from the fluid.

37. The process according to claim 36, wherein the fluid is water.

38. The process according to claim 36, wherein the fluid is removed by freeze drying or spray drying.

39. The process according to claim 36, wherein the fluid is removed in a fluidized bed process.

40. The process according to claim 36, wherein fluid is removed from a fluid-comprising mixture comprising components (a), (b) and (e).

41. The process according to claim 36, wherein a solid comprising components (a) and (b) is introduced, a fluid-comprising mixture comprising component (e) is added and fluid is removed.

42. The process according to claim 41, wherein the fluid-comprising mixture is a concentrate comprising at least 5% by weight of component (e).

43. The process according to claim 36, wherein a solid comprising component (e) is introduced, a fluid-comprising mixture comprising components (a) and (b) is added and fluid is removed.

44. A process of for the preparation of a solution, dispersion or emulsion (spray mixture) for the fungicidal, insecticidal or herbicidal treatment of plants and/or their habitat which comprises dissolving, dispersing or emulsifying a solid plant protection composition according to claim 1 in water.

45. A process for the fungicidal, insecticidal or herbicidal treatment of plants and their habitat, wherein a solid plant protection composition according to claim 1 is dissolved, dispersed or emulsified and plants and/or their habitat are treated with the resulting solution, dispersion or emulsion spray mixture.

46. The process according to claim 45, wherein the dissolving, dispersing or emulsifying is carried out in a tank mix method.

47. The process according to claim 45, wherein the treatment is carried out in a spray method.

48. A spray mixture, comprising a plant protection composition according to claim 1.

49. The spray mixture according to claim 48, comprising from 0.0001 to 10% by weight of the plant protection active agent.

* * * * *